(12) United States Patent
Yoshida et al.

(10) Patent No.: US 7,420,065 B2
(45) Date of Patent: Sep. 2, 2008

(54) HETERO-POLYCYCLIC COMPOUNDS, AND COLORING MATTERS, PIGMENTS, DYES, COLOR-CHANGING MATERIAL COMPOSITIONS, AND COLOR-CHANGING FILMS, MADE BY USING THE COMPOUNDS

(75) Inventors: Katsuhira Yoshida, Kochi (JP); Yousuke Ooyama, Kochi (JP); Satoshi Hachiya, Chiba (JP)

(73) Assignees: Idemitsu Kosan Co., Ltd., Tokyo (JP); Techno Network Shikoku Co., Ltd., Takamatsu-shi (JP)

( * ) Notice: Subject to any disclaimer, the term of this patent is extended or adjusted under 35 U.S.C. 154(b) by 221 days.

(21) Appl. No.: 10/545,319

(22) PCT Filed: Feb. 12, 2004

(86) PCT No.: PCT/JP2004/001472

§ 371 (c)(1),
(2), (4) Date: Mar. 28, 2006

(87) PCT Pub. No.: WO2004/072053

PCT Pub. Date: Aug. 26, 2004

(65) Prior Publication Data

US 2006/0235060 A1 Oct. 19, 2006

(30) Foreign Application Priority Data

Feb. 14, 2003 (JP) ............................ 2003-036738
Feb. 14, 2003 (JP) ............................ 2003-036790

(51) Int. Cl.
*C07D 307/77* (2006.01)
*C07D 333/50* (2006.01)
*C07D 495/00* (2006.01)
*C07D 209/80* (2006.01)

(52) U.S. Cl. .................... 549/457; 549/42; 549/24; 548/420

(58) Field of Classification Search .................... 549/42, 549/24, 457; 548/420, 149, 218, 301.7
See application file for complete search history.

(56) References Cited

U.S. PATENT DOCUMENTS 2,783,248 A * 2/1957 Brunnstrom ................ 549/456

FOREIGN PATENT DOCUMENTS

| | | |
|---|---|---|
| EP | 0 600 667 A1 | 6/1994 |
| EP | 0 600 668 | 6/1994 |
| JP | 11-124572 | 5/1999 |
| JP | 2003-217857 | 7/2003 |
| JP | 2003-229274 | 8/2003 |
| JP | 2004-006064 | 1/2004 |
| WO | 99/20630 | 4/1999 |

* cited by examiner

*Primary Examiner*—Cecilia Tsang
*Assistant Examiner*—Kristin Bianchi
(74) *Attorney, Agent, or Firm*—Oblon, Spivak, McClelland, Maier & Neustadt, P.C.

(57) ABSTRACT

Provided are novel hetero-polycyclic compounds having a specific structure, color-changing material compositions comprising (A) a fluorescent coloring matter comprising at least one of the hetero-polycyclic compounds described above and (B) a binder material, color-changing films comprising the above hetero-polycyclic compounds, coloring matters comprising the above hetero-polycyclic compounds, and pigments or dyes comprising the hetero-polycyclic compounds described above, and provided are color-changing material compositions which are not deteriorated in a color-changing performance even after used for long time and which are prevented from being unusable due to deposition of coloring matters during storage and color-changing films produced by using the same, and novel hetero-polycyclic compounds, coloring matters and pigments or dyes which actualize them.

3 Claims, 3 Drawing Sheets

HETERO-POLYCYCLIC COMPOUNDS, AND COLORING MATTERS, PIGMENTS, DYES, COLOR-CHANGING MATERIAL COMPOSITIONS, AND COLOR-CHANGING FILMS, MADE BY USING THE COMPOUNDS

BACKGROUND OF THE INVENTION

The present invention relates to novel hetero-polycyclic compounds, and coloring matters, pigments or dyes, color-changing material compositions and color-changing films, which are produced by using the above compounds, specifically to color-changing material compositions which are not deteriorated in a color-changing performance even after used for long time and which are prevented from being unusable due to deposition of coloring matters during storage and color-changing films produced by using the same, and novel hetero-polycyclic compounds, coloring matters and pigments or dyes which actualize them.

RELATED ART

Organic fluorescent coloring matters have so far been used in the wide fields as coloring matters for fluorescence-changing films in various display equipments and as coloring matters for dye lasers, copy prevention, solar energy changing and fluorescent films in green houses, in addition to uses as dyes and pigments.

The organic fluorescent coloring matters used for the above applications are strongly desired to be controlled in a fluorescent wavelength in a solid state and improved in a luminous intensity. However, it is known that in general, a fluorescent intensity of an organic fluorescent coloring matter in a solid state is weak as compared with the fluorescent intensity thereof in a solution state. It is the existing situation that this phenomenon is neglected as concentration quenching and that the details thereof are not known well. This is because it has been difficult in conventional organic fluorescent coloring matters to allow a molecular packing structure in a crystal lattice to variously change to investigate an influence thereof exerted to light absorption and a fluorescent property of an organic fluorescent coloring matter in a solid state.

The present inventors have created previously as substances for solving the above points, novel fluorescent coloring matters having a clathrate-forming ability capable of changing an intrinsic color and a fluorescent luminescence which the coloring matters are endowed with to a large extent by allowing various organic low molecular compounds (organic guest molecules) to be included therein in a solid state (refer to, for example, "Chem. Lett.", p. 9 (1996), "Chem. Lett.", p. 837 (1999), "Chem. Lett.", p. 714 (2000), "Chem. Lett.", p. 808 (2001) and "J. Chem. Perkin Trans.", vol. 2, p. 700 to 714 and p. 708 to 714 (2002)). Use of the above fluorescent coloring matters having a clathrate-forming ability makes it possible to variously change orientation and arrangement of the coloring matter molecules on a molecular level by allowing organic guest molecules to be included therein, and this makes it possible to change the solid optical properties (color tone and fluorescent property) of the coloring matters to a large extent.

Accordingly, utilization of the above characteristics makes it possible to obtain basic knowledge regarding correlation between a packing structure of coloring matter molecules and light absorption and fluorescent luminescence thereof in a solid state, which has not yet sufficiently been clarified, and this makes it possible to create fluorescent organic solid materials having optical properties which meet various needs.

Organic electroluminescent elements (hereinafter referred to as organic EL elements) are completely solid elements and can produce displays which are light-weight and thin and which are driven at low voltage, and therefore they are actively researched in various fields at present. In particular, the largest technical subject for producing displays from organic EL elements is development of a full colorization method. Light emissions of blue, green and red colors have to be finely arranged in order to produce such full color displays, and three methods of a three-color separate coating method, a color filter method and a color-changing method are considered as the method therefor at present.

Among them, the color-changing method makes it easy to produce large-scaled displays as compared with the three-color separate coating method, and it has the advantage that a loss in the luminance is small as compared with that in the color filter method. Accordingly, the present inventors have been investigating full colorization of organic EL elements by the color-changing method.

When producing a full color display by using this color-changing method, a color-changing film used for changing a blue color emitted to a green color and a red color has to be finely patterned. Further, a color-changing film is constituted from a fluorescent coloring matter and a resin for dispersing it, and a fine processing property is required to this resin itself in order to highly finely pattern the film. In order to meet the above purposes, color-changing material compositions prepared by using basic resins such as vinylpyridine derivatives and aminostyrene derivatives are used in, for example, Japanese Patent Application Laid-Open No. 208944/1997; color-changing material compositions prepared by using ethylenically unsaturated carboxylic acid copolymers are disclosed in Japanese Patent Application Laid-Open No. 106888/1997; and color-changing material compositions comprising unsaturated group-containing compounds obtained by reacting polybasic carboxylic acids or anhydrides thereof with reaction products of epoxy compounds and acrylic acid or methacrylic acid and at least one fluorescent substance selected from fluorescent coloring matters and fluorescent pigments are disclosed in Japanese Patent Application Laid-Open No. 119645/2000.

However, the above color-changing material compositions have had the problems that when a color-changing film containing a coumarin base coloring matter as a coloring matter absorbing blue light is continued to be irradiated with blue light emitted from an organic EL, the coumarin base coloring matter is decomposed and can not sufficiently absorb blue light of a light source to allow it to be transmitted and that the color-changing property is deteriorated or the coloring matter is deposited during storage depending on the resin composition to make it impossible to use the film.

DISCLOSURE OF THE INVENTION

The present invention has been made in order to solve the problems described above, and a an object of the present invention is to provide a novel hetero-polycyclic compound which functions as a conventional organic coloring matter and organic fluorescent coloring matter or as an organic fluorescent coloring matter having a clathrate-forming ability and a fluorescent property and capable of changing the solid optical properties (color tone and fluorescent property) of the coloring matter to a large extent by allowing organic guest molecules to be included therein and which is suitably used for various applications, and a coloring matter and a pigment or a dye which are prepared by using the above compound. Further, an object of the present invention is to provide a color-changing material composition prepared by using the above compound, which is not deteriorated in a color-changing performance even after used for long time and which is prevented from being unusable due to deposition of the coloring matter during storage, and a color-changing film produced by using the same.

Intensive researches repeated by the present inventors in order to achieve the objects described above have resulted in finding that the objects described above can be achieved by using hetero-polycyclic compounds having the specific structures represented by the following Formulas (I) and (II) as coloring matters and the following Formulas (III) to (VIII) as fluorescent coloring matters.

That is, the present invention provides a hetero-polycyclic compound represented by any of the following Formulas (I) to (VIII):

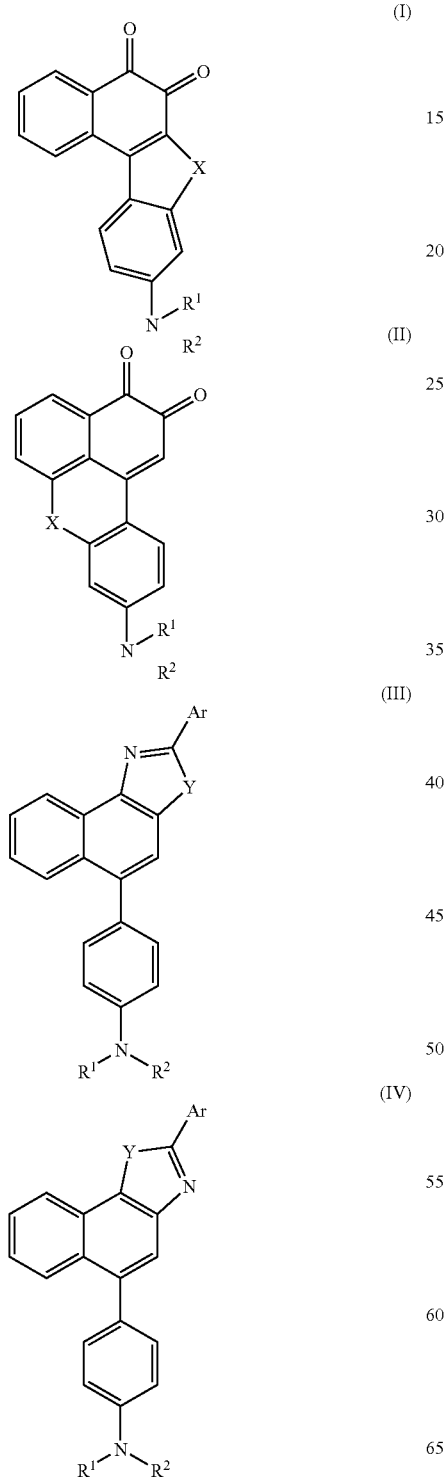

wherein $R^1$ and $R^2$ each represent independently an alkyl group having 1 to 10 carbon atoms which may have a substituent, an arylalkyl group having 7 to 30 carbon atoms which may have a substituent, an aryl group having 6 to 20 carbon atoms which may have a substituent or a heteroaryl group having 5 to 20 carbon atoms which may have a substituent, and they may be combined with each other to form a cyclic structure or may form a cyclic structure together with a benzene ring to which a nitrogen atom is bonded;

X represents an oxygen atom, a sulfur atom, —NH— or —NR³— (R³ represents an alkyl group having 1 to 10 carbon atoms which may have a substituent, an aryl group having 6 to 20 carbon atoms which may have a substituent or a heteroaryl group having 5 to 20 carbon atoms which may have a substituent);

Y represents an oxygen atom, a sulfur atom, —NH— or —NR⁴— (R⁴ represents an alkyl group having 1 to 10 carbon atoms which may have a substituent, an aryl group having 6 to 20 carbon atoms which may have a substituent or a heteroaryl group having 5 to 20 carbon atoms which may have a substituent), provided that Y represents an oxygen atom, a sulfur atom or —NR⁴— in Formulas (III) and (IV); and Ar represents an aryl group having 6 to 20 carbon atoms which may have a substituent or a heteroaryl group having 5 to 20 carbon atoms which may have a substituent.

Further, the resent invention provides a color-changing material composition comprising (A) a fluorescent coloring matter comprising at least one of the hetero-polycyclic compounds represented by Formulas (III) to (VIII) and (B) a binder material, and a color-changing film comprising the above color-changing material composition.

Further, the resent invention provides a coloring matter comprising the hetero-polycyclic compound described above and a pigment or a dye containing the hetero-polycyclic compound described above.

BRIEF DESCRIPTIONS OF THE DRAWINGS

Figure 1:
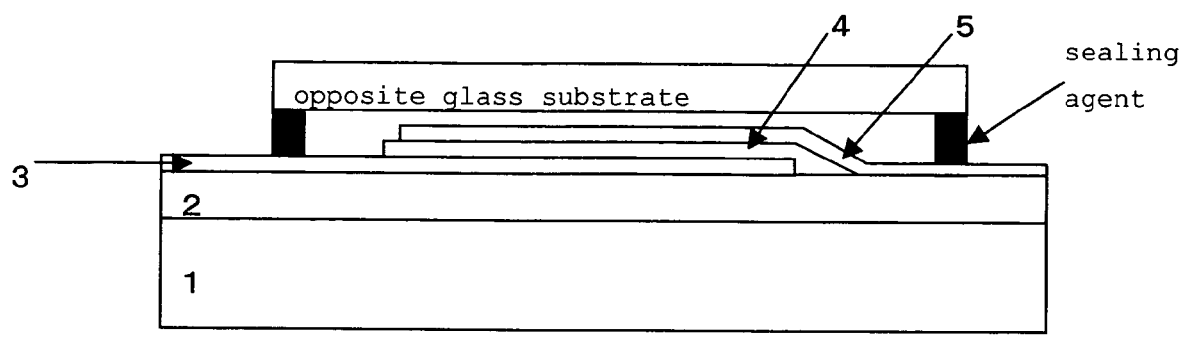
FIG. 1 is a drawing showing a structure of a colorized organic EL element used for evaluating a color-changing performance in the examples and the comparative examples.

A number 1 is a glass substrate; 2 is a color-changing film; 2 is an anode; 4 is an organic EL luminescent layer; and 5 is a cathode.

BEST MODE FOR CARRYING OUT THE INVENTION

The hetero-polycyclic compound of the present invention is a novel hetero-polycyclic compound which has a structure represented by any of the following Formulas (I) to (VIII) and which is not described in documents:

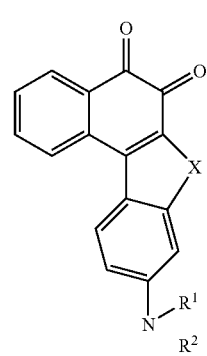

(I)

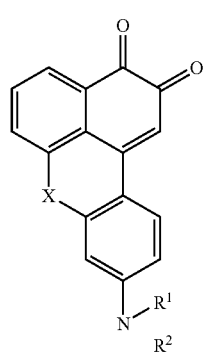

(II)

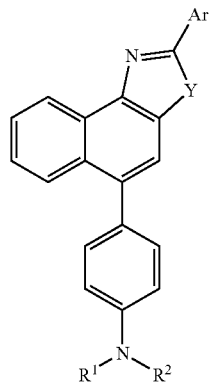

(III)

(IV) 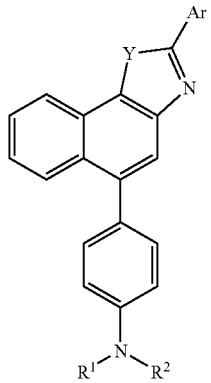

(V)

(VI)

(VII)

(VIII) 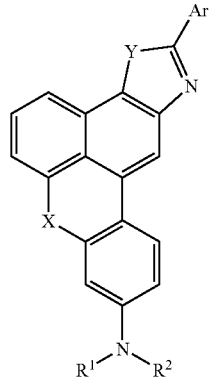

In Formulas (I) to (VIII), $R^1$ and $R^2$ each represent independently an alkyl group having 1 to 10 carbon atoms which may have a substituent, an arylalkyl group having 7 to 30 carbon atoms which may have a substituent, an aryl group having 6 to 20 carbon atoms which may have a substituent or a heteroaryl group having 5 to 20 carbon atoms which may have a substituent, and they may be combined with each other to form a cyclic structure or may form a cyclic structure together with a benzene ring to which a nitrogen atom is bonded.

The alkyl group described above may be any of linear, branched and cyclic groups, and the examples thereof include methyl, ethyl, n-propyl, isopropyl, various butyls, various pentyls, various hexyls, various octyls, various decyls, cyclopentyl, cyclohexyl, cyclooctyl, benzyl and phenethyl.

The examples of the arylalkyl group described above include benzyl, 1-phenylethyl, 2-phenylethyl, 1-phenylisopropyl, 2-phenylisopropyl, phenyl-t-butyl, α-naphthylmethyl, 1-α-naphthylethyl, 2-α-naphthylethyl, 1-α-naphthylisopropyl, 2-α-naphthylisopropyl, β-naphthylmethyl, 1-β-naphthylethyl, 2-α-naphthylethyl, 1-β-naphthylisopropyl, 2-β-naphthylisopropyl, 1-pyrrolylmethyl, 2-(1-pyrrolyl)ethyl, p-methylbenzyl, m-methylbenzyl, o-methylbenzyl, p-chlorobenzyl, m-chlorobenzyl, o-chlorobenzyl, p-bromobenzyl, m-bromobenzyl, o-bromobenzyl, p-iodobenzyl, m-iodobenzyl, p-iodobenzyl, p-hydroxybenzyl, m-hydroxybenzyl, o-hydroxybenzyl, p-aminobenzyl, m-aminobenzyl, o-aminobenzyl, p-nitrobenzyl, m-nitrobenzyl, o-nitrobenzyl, p-cyanobenzyl, m-cyanobenzyl, o-cyanobenzyl, 1-hydroxy-2-phenylisopropyl and 1-chloro-2-phenylisopropyl.

The examples of the aryl group described above include phenyl, naphthyl, anthryl and pyrenyl.

The examples of the heteroaryl group described above include 1-aza-indolizine-2-yl, 1-aza-indolizine-3-yl, 1-aza-indolizine-5-yl, 1-aza-indolizine-6-yl, 1-aza-indolizine-7-yl, 1-aza-indolizine-8-yl, 2-aza-indolizine-1-yl, 2-aza-indolizine-3-yl, 2-aza-indolizine-5-yl, 2-aza-indolizine-6-yl, 2-aza-indolizine-7-yl, 2-aza-indolizine-8-yl, 6-aza-indolizine-1-yl, 6-aza-indolizine-2-yl, 6-aza-indolizine-3-yl, 6-aza-indolizine-5-yl, 6-aza-indolizine-7-yl, 6-aza-indolizine-8-yl, 7-aza-indolizine-1-yl, 7-aza-indolizine-2-yl, 7-aza-indolizine-3-yl, 7-aza-indolizine-5-yl, 7-aza-indolizine-6-yl, 7-aza-indolizine-7-yl, 7-aza-indolizine-8-yl, 8-aza-indolizine-1-yl, 8-aza-indolizine-2-yl, 8-aza-indolizine-3-yl, 8-aza-indolizine-5-yl, 8-aza-indolizine-6-yl, 8-aza-indolizine-7-yl, 1-indolizinyl, 2-indolizinyl, 3-indolizinyl, 5-indolizinyl, 6-indolizinyl, 7-indolizinyl, 8-indolizinyl, 1-pyrrolyl, 2-pyrrolyl, 3-pyrrolyl, pyrazinyl, 2-pyridinyl, 3-pyridinyl, 4-pyridinyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 9-carbazolyl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 1,7-phenanthroline-2-yl, 1,7-phenanthroline-3-yl, 1,7-phenanthroline-4-yl, 1,7-phenanthroline-5-yl, 1,7-phenanthroline-6-yl, 1,7-phenanthroline-8-yl, 1,7-phenanthroline-9-yl, 1,7-phenanthroline-10-yl, 1,8-phenanthroline-2-yl, 1,8-phenanthroline-3-yl, 1,8-phenanthroline-4-yl, 1,8-phenanthroline-5-yl, 1,8-phenanthroline-6-yl, 1,8-phenanthroline-7-yl, 1,8-phenanthroline-9-yl, 1,8-phenanthroline-10-yl, 1,9-phenanthroline-2-yl, 1,9-phenanthroline-3-yl, 1,9-phenanthroline-4-yl, 1,9-phenanthroline-5-yl, 1,9-phenanthroline-6-yl, 1,9-phenanthroline-7-yl, 1,9-phenanthroline-8-yl, 1,9-phenanthroline-10-yl, 1,10-phenanthroline-2-yl, 1,10-phenanthroline-3-yl, 1,10-phenanthroline-4-yl, 1,10-phenanthroline-5-yl, 2,9-phenanthroline-1-yl, 2,9-phenanthroline-3-yl, 2,9-phenanthroline-4-yl, 2,9-phenanthroline-5-yl, 2,9-phenanthroline-6-yl, 2,9-phenanthroline-7-yl, 2,9-phenanthroline-8-yl, 2,9-phenanthroline-10-yl, 2,8-phenanthroline-1-yl, 2,8-phenanthroline-3-yl, 2,8-phenanthroline-4-yl, 2,8-phenanthroline-5-yl, 2,8-phenanthroline-6-yl, 2,8-phenanthroline-7-yl, 2,8-phenanthroline-9-yl, 2,8-phenanthroline-10-yl, 2,7-phenanthroline-1-yl, 2,7-phenanthroline-3-yl, 2,7-phenanthroline-4-yl, 2,7-phenanthroline-5-yl, 2,7-phenanthroline-6-yl, 2,7-phenanthroline-8-yl, 2,7-phenanthroline-9-yl, 2,7-phenanthroline-10-yl, 1-phenazinyl, 2-phenazinyl, 1-phenothiazinyl, 2-phenothiazinyl, 3-phenothiazinyl, 4-phenothiazinyl, 10-phenothiazinyl, 1-phenoxazinyl, 2-phenoxazinyl, 3-phenoxazinyl, 4-phenoxazinyl, 10-phenoxazinyl, 2-oxazolyl, 4-oxazolyl, 5-oxazolyl, 2-oxadiazolyl, 5-oxadiazolyl, 3-frazanyl, 2-thienyl, 3-thienyl, 2-methylpyrrole-1-yl, 2-methylpyrrole-3-yl, 2-methylpyrrole-4-yl, 2-methylpyrrole-5-yl, 3-methylpyrrole-1-yl, 3-methylpyrrole-2-yl, 3-methylpyrrole-4-yl, 3-methylpyrrole-5-yl, 2-t-butylpyrrole-4-yl, 3-(2-phenylpropyl)pyrrole-1-yl, 2-methyl-1-indolyl, 4-methyl-1-indolyl, 2-methyl-3-indolyl, 4-methyl-3-indolyl, 2-t-butyl-1-indolyl, 4-t-butyl-1-indolyl, 2-t-butyl-3-indolyl and 4-t-butyl-3-indolyl.

The above respective groups may have suitable substituents, and the substituents include, for example, an alkyl group, an alkoxyl group, a halogen atom, a cyano group, an alkoxycarbonyl group, a carboxyl group, an ester group, an amide group, a sulfoxyl group, a sulfonamide group, a nitro group, an aryl group and a heteroaryl group.

The examples of the above alkyl group, aryl group and heteroaryl group include the same groups as described above. The examples of the halogen atom include a fluorine atom, a chlorine atom, a bromine atom and an iodine atom. The alkoxyl group may be any of linear, branched and cyclic groups, and the examples thereof include methoxy, ethoxy, n-propoxy, isopropoxy, various butoxy, various pentoxy, various hexoxy, various octoxy, various decyloxy, cyclopenthyloxy, cyclohexyloxy, benzyloxy and phenethyloxy. The sulfonamide group may be either of substituted sulfonamide and non-substituted sulfonamide, and the amide group may be either of substituted amide and non-substituted amide. Substituents for the above alkoxyl group, sulfonamide group and amide group include the same groups as given in $R^1$ and $R^2$ described above. Further, the examples of an alkoxyl group in the alkoxycarbonyl group include the same groups as described above.

The cyclic structure formed by allowing $R^1$ and $R^2$ to be combined with each other together with a nitrogen atom includes, for example, 1-pyrrolidinyl, piperidino and morpholine.

The cyclic structure formed by allowing $R^1$ and $R^2$ to be combined with each other together with a benzene ring to which a nitrogen atom is bonded includes, for example, the following ones:

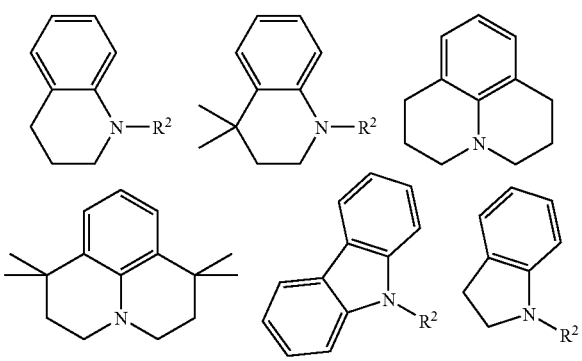

In Formulas (I), (II) and (V) to (VIII), X represents an oxygen atom, a sulfur atom, —NH— or —$NR^3$— ($R^3$ represents an alkyl group having 1 to 10 carbon atoms which may have a substituent, an aryl group having 6 to 20 carbon atoms which may have a substituent or a heteroaryl group having 5 to 20 carbon atoms which may have a substituent).

The examples of the alkyl group, the aryl group and the heteroaryl group represented by $R^3$ described above each include the same groups as given in $R^1$ and $R^2$ described above, and the substituents therefor include as well the same groups.

In Formulas (III) and (IV), Y represents an oxygen atom, a sulfur atom or —$NR^4$— ($R^4$ represents an alkyl group having 1 to 10 carbon atoms which may have a substituent, an aryl group having 6 to 20 carbon atoms which may have a substituent or a heteroaryl group having 5 to 20 carbon atoms which may have a substituent), and in Formulas (V) to (IV), Y represents an oxygen atom, a sulfur atom, —NH— or —$NR^4$— ($R^4$ is the same as described above).

The examples of the alkyl group, the aryl group and the heteroaryl group represented by $R^4$ described above include the same groups as given respectively in $R^1$ and $R^2$ described above, and substituents therefor include as well the same groups.

In Formulas (III) to (VIII), Ar represents an aryl group having 6 to 20 carbon atoms which may have a substituent or a heteroaryl group having 5 to 20 carbon atoms which may have a substituent. The examples of the aryl group and the heteroaryl group each include the same groups as given in $R^1$ and $R^2$ described above, and the substituents therefor include as well the same groups.

The specific example of the compound represented by Formula (I) described above includes, for example, a compound represented by the following Formula (I-a):

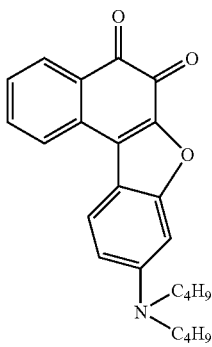

(I-a)

The specific example of the compound represented by Formula (II) described above includes, for example, a compound in which a ring formed by X assumes a six-membered structure represented by Formula (II) in the compound represented by Formula (I-a).

The compounds of the present invention represented by Formula (I) and Formula (II) are coloring matters and can suitably be used as disperse dyes, coloring matters for ink-jet printing, electrophotographic toners, heat transfer coloring matters, non-linear optical materials such as light modulation elements, photoelectric transfer coloring matters such as organic solar batteries and high density optical recording type coloring matters each containing the above coloring matters. Further, they can also be used as intermediates for producing the following compounds of the present invention represented by Formula (V) to Formula (VIII).

Compounds represented by Formula (III-a) to Formula (III-d) can be given as the specific examples of the compound of the present invention represented by Formula (III):

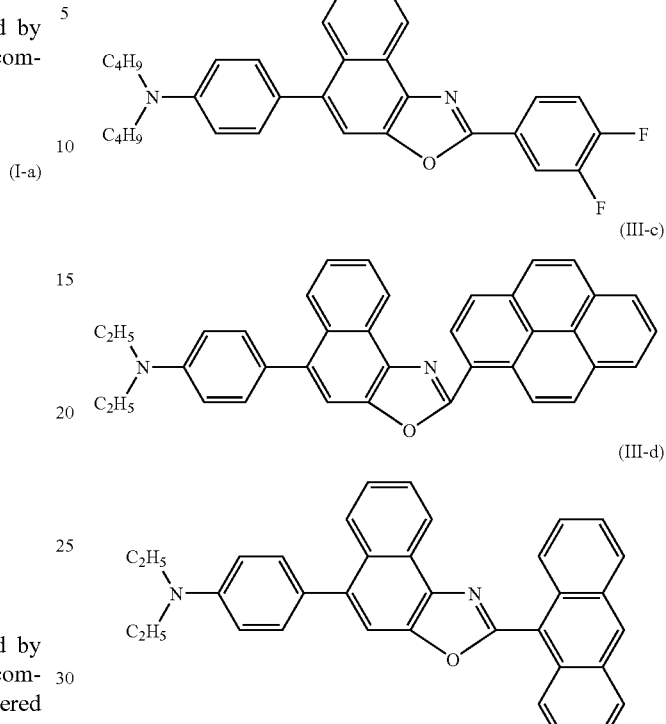

Compounds represented by Formula (IV-a) to Formula (IV-d) can be given as the specific examples of the compound of the present invention represented by Formula (IV):

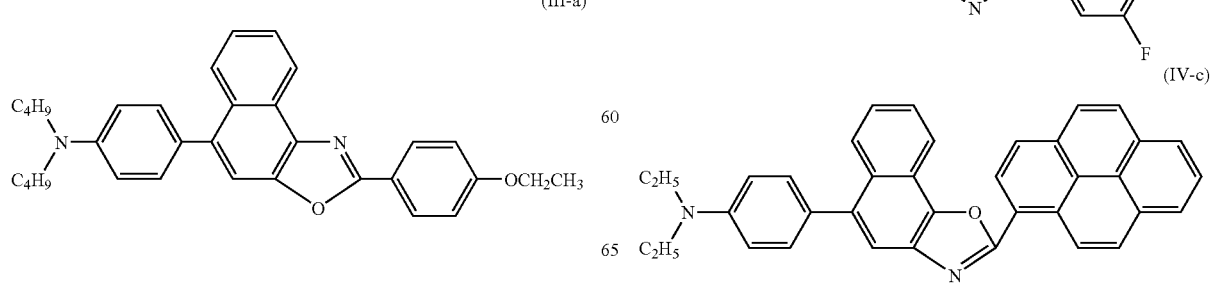

-continued (IV-d)

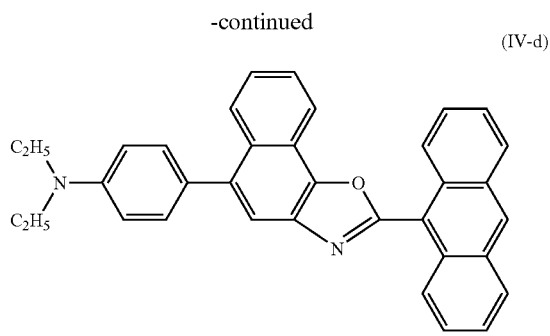

Compounds represented by Formula (V-a) to Formula (V-c) can be given as the specific examples of the compound of the present invention represented by Formula (V):

(V-a)

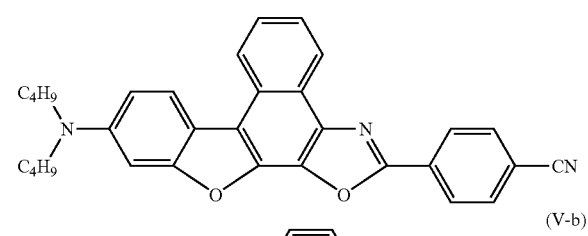

(V-b)

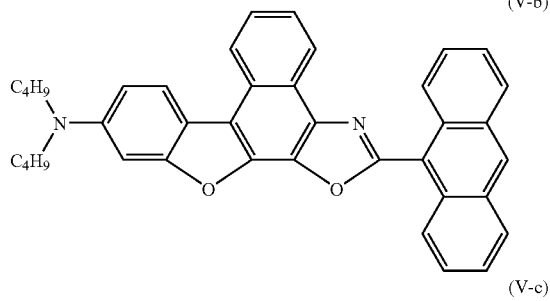

(V-c)

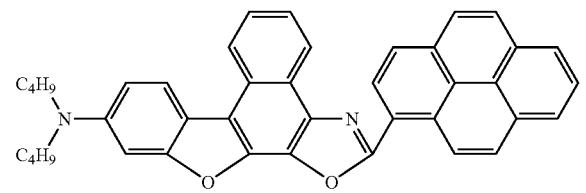

Compounds represented by Formula (VI-a) to Formula (VI-c) can be given as the specific examples of the compound of the present invention represented by Formula (VI):

(VI-a)

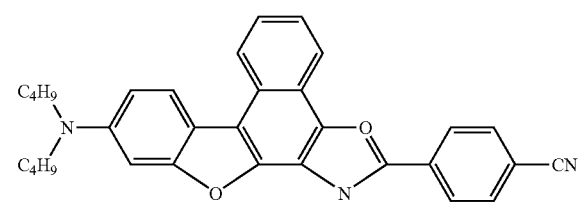

-continued (VI-b)

(VI-c)

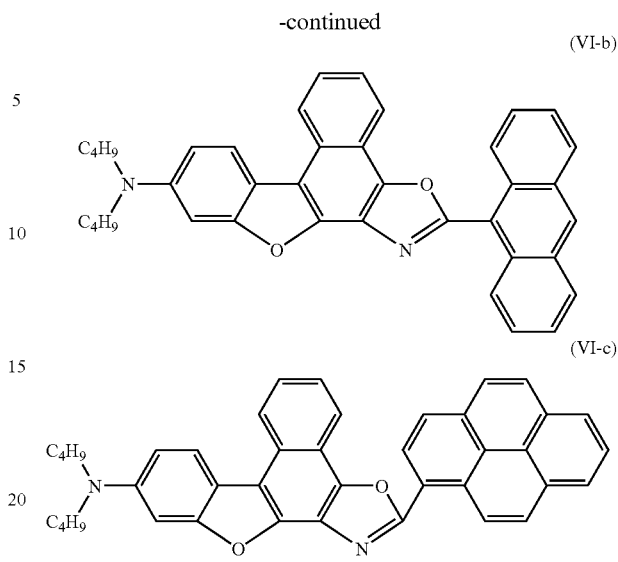

The specific examples of the compound represented by Formula (VII) described above include, for example, compounds in which a ring formed by X assumes a six-membered structure represented by Formula (VII) in the compounds represented by (V-a) to (V-c) described above.

The specific examples of the compound represented by Formula (VIII) described above include, for example, compounds in which a ring formed by X assumes a six-membered structure represented by Formula (VIII) in the compounds represented by (VI-a) to (VI-c) described above.

The compounds of the present invention represented by Formula (III) to Formula (VIII) are organic fluorescent coloring matters and can suitably be used as disperse dyes, coloring matters for ink-jet printing, electrophotographic toners, heat transfer coloring matters, luminescent materials such as organic electroluminescent elements, non-linear optical materials such as light modulation elements, photoelectric transfer coloring matters such as organic solar batteries, fluorescent coloring matters such as organic EL•dye lasers, modulated light•wavelength transfer coloring matters such as agricultural films, high density optical recording type coloring matters and fluorescent coloring matters for molecular recognition each containing the above coloring matters. Further, some compounds have a clathrate-forming ability, and they can be derived as well into solid-luminescent organic fluorescent coloring matters comprising clathrate complexes in which a color tone and a fluorescent luminescence are changed and in which performances are raised further more by allowing various organic guest molecules to be included therein.

The compounds of the present invention represented by Formula (III) to Formula (VIII) and the clathrate complexes thereof can be used for various applications as the organic fluorescent coloring matters, for example, fluorescence-changing films in various display equipments, coloring matter laser, light toning, energy changing, high density optical recording, display and fluorescent sensors for molecular recognition.

Among the applications described above, the fluorescence-changing films in various display equipments can be applied to electronic display devices such as, for example, PDP (plasma display), ELD (electroluminescence display), LED (light-emitting diode) and VFD (fluorescent display tube).

Next, a production process for the hetero-polycyclic compound of the present invention shall be explained.

A production process for the compound represented by Formula (I) shall be explained.

The hetero-polycyclic compound of the present invention represented by Formula (I) which is a 1,2-naphthoquinone base derivative can be produced according to, for example, a reaction equation (A) shown below when X is an oxygen atom:

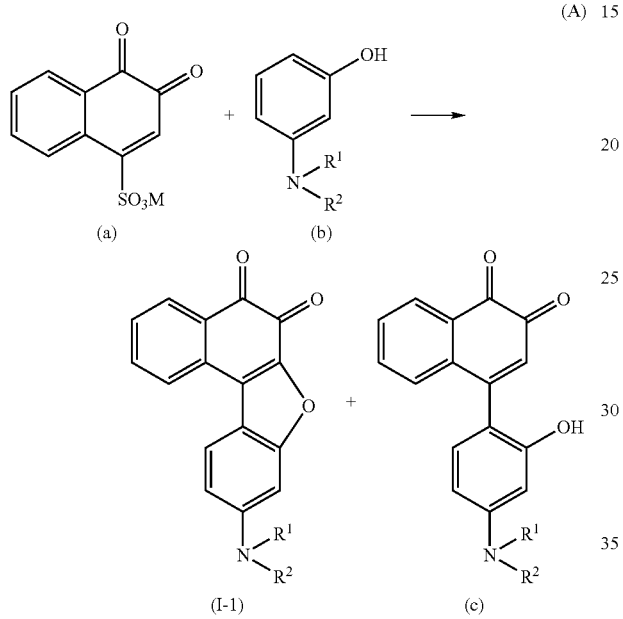

wherein M represents an alkali metal atom, and $R^1$ and $R^2$ are the same as described above.

As shown in the reaction equation (A), the substantially stoichiometric amounts of 1,2-naphthoquinone-4-sulfonic acid alkali metal salt (a) and m-substituted phenol (b) are reacted at a temperature of about 0 to 80° C. in a suitable solvent such as acetic acid in the presence of a catalyst such as copper (II) halide, whereby a compound which has a benzofurano-1,2-naphthoquinone skeleton represented by Formula (I-1) and in which X is an oxygen atom. In this case, a compound represented by Formula (c) is by-produced.

With respect to a production process for the compound of the present invention represented by Formula (II), the compound represented by Formula (c) is obtained as a principal component by using a catalyst having a weak oxidizing strength such as nickel chloride in the above reaction equation (A), and after isolating the compound represented by Formula (c), cyclization reaction is carried out at a temperature of about 40 to 120° C. in a solvent such as dimethylsulfoxide in the presence of a catalyst having a strong oxidizing strength such as copper acetate, whereby the above compound represented by Formula (II) can be produced.

With respect to a production process for the compounds of the present invention represented by Formula (III) and (IV), they can be produced according to a reaction equation (B) shown below, for example, when Y is an oxygen atom:

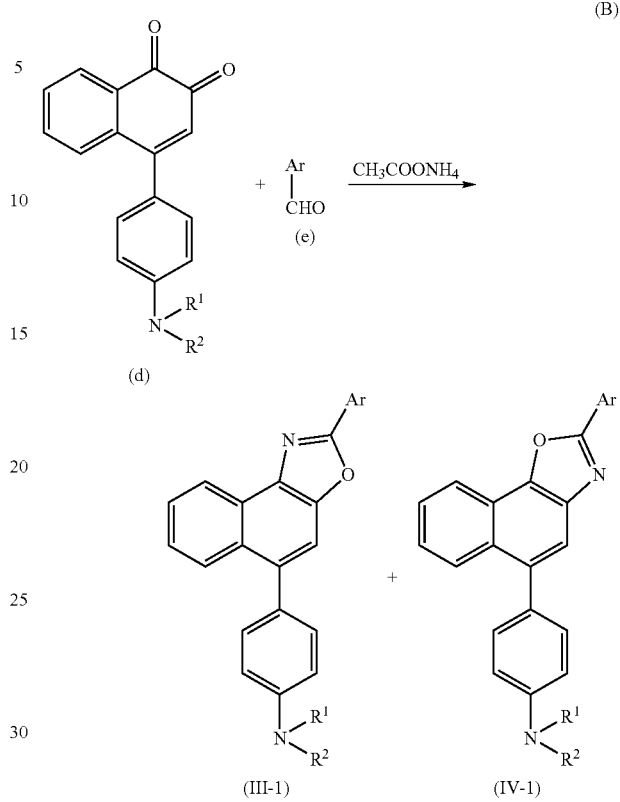

wherein $R^1$, $R^2$ and Ar are the same as described above.

As shown in the reaction equation (B), a 1,2-naphthoquinone derivative represented by Formula (d) is reacted with a substantially stoichiometric amount or a little excessive amount of arylaldehyde (e) and an excessive amount of ammonium acetate in a suitable solvent such as acetic acid at a temperature of about 50 to 100° C., whereby compounds represented by Formula (III-1) and (IV-1) having a naphthoxazole skeleton are obtained.

With respect to a production process for the compounds of the present invention represented by Formula (V) and (VI), they can be produced according to a reaction equation (C) shown below, for example, when X and Y each are oxygen atoms:

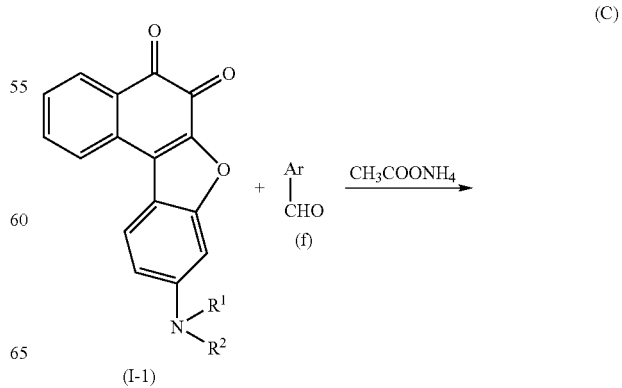

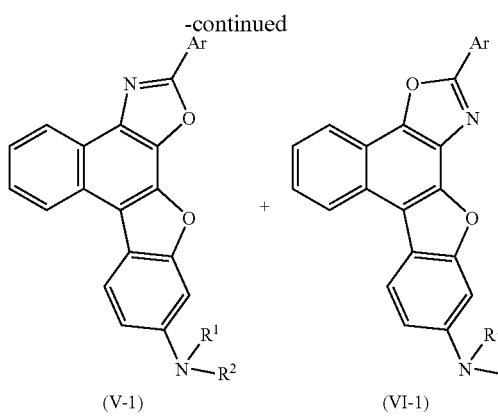

(V-1)          (VI-1)

wherein $R^1$, $R^2$ and Ar are the same as described above.

As shown in the reaction equation (C), the compound represented by Formula (I-1) is reacted with a little excessive amount of arylaldehyde (f) and an excessive amount of ammonium acetate in a suitable solvent such as acetic acid at a temperature of about 50 to 100° C., whereby compounds having a benzofuranonaphthoxazole skeleton represented by Formula (V-1) and (VI-1) are obtained.

With respect to a production process for the compounds of the present invention represented by Formula (VII) and (VIII), they can be produced by using the compound represented by Formula (II) in place of the compound represented by Formula (I-1).

The color-changing material composition of the present invention shall be explained below.

The color-changing material composition of the present invention comprises (A) a fluorescent coloring matter comprising at least one of the hetero-polycyclic compounds represented by Formulas (III) to (VIII) described above and (B) a binder material.

A concentration of the component (A) described above shall not specifically be restricted, and it is preferably 0.1 to 10% by weight, more preferably 0.2 to 5% by weight based on the whole amount of the solid matters contained in the color-changing material composition. If the concentration is 0.1 by weight or more, light can sufficiently be absorbed from a light source, and the color can be changed. If it is 10 by weight or less, it is prevented that the color-changing efficiency is reduced due to concentration quenching and that highly fine patterning can not be carried out.

The binder material of the component (B) is more preferably an optically reactive resin. In this case, the optically reactive resin means a resin which shows curing reaction by light, and it includes resins blended with polymerizable oligomers and/or monomers such as epoxy acrylate, urethane acrylate and polyether acrylate and resins blended with allyl-sulfonyl salts and epoxy compounds.

The binder material of the component (B) is preferably a thermosetting resin or a thermoplastic resin.

The thermosetting resin includes, for example, epoxy resins, urethane resins, alkid resins and polyimide resins, and the epoxy resins and the urethane resins are particularly preferred since they have a high transparency and a high dispersibility of coloring matters.

The thermoplastic resin includes, for example, (meth)acryl resins, polystyrene resins, polycarbonate resins and polyester resins, and the (meth)acryl resins and the polycarbonate resins are particularly preferred since they have a high transparency and a high dispersibility of coloring matters.

The color-changing material composition of the present invention contains more preferably a Rhodamine base fluorescent coloring matter such as Rhodamine B and Rhodamine 6G.

Further, the binder material (B) used in the present invention contains preferably (C) a methacrylic acid ester-methacrylic acid copolymer and (D) a monomer and/or oligomer having a photopolymerizable, ethylenically unsaturated group.

The methacrylic acid ester-methacrylic acid copolymer (C) described above is represented by a structure shown below:

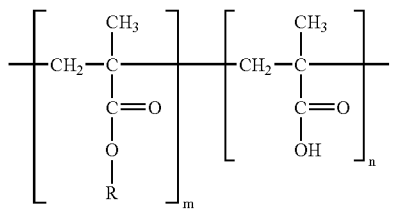

R is a substituted or non-substituted alkyl group having 1 to 10 carbon atoms or a substituted or non-substituted aryl group having 6 to 20 carbon atoms, and it includes, for example, benzyl, methyl, ethyl, cyclohexyl, cyclohexylmethyl and hydroxyethyl. R is preferably methyl or benzyl since the solubility, the developability and the film quality are balanced. The terms m and n each are preferably an integer of 1 or more. The above copolymer has a molecular weight of preferably 5,000 to 100,000, more preferably 10,000 to 50,000 in terms of Mw (weight average molecular weight). If Mw is 5,000 or more, the color-changing film is not reduced in a strength. If it is 100,000 or less, a viscosity of the solution is not excessive, and the even color-changing film is formed.

The copolymerization ratio q is preferably $q=m/(m+n)=0.5$ to 0.95, more preferably 0.7 to 0.9. If the copolymerization ratio is 0.5 or more, the film is not swollen by a developing solution in developing, and the patterning accuracy is not reduced. If it is 0.95 or less, the solubility in a developing solution does not become too small, and a case where developing can not be carried out is prevented.

The monomer and/or oligomer (D) having a photopolymerizable, ethylenically unsaturated group includes 2-hydroxyethyl (meth)acrylate, 2-hydroxypropyl (meth)acrylate and 2-hydroxyhexyl (meth)acrylate.

The examples of the (meth)acrylate described above include ethylene glycol di(meth)acrylate, diethylene glycol di(meth)acrylate, triethylene glycol di(meth)acrylate, tetraethylene glycol di(meth)acrylate, tetramethylene glycol di(meth)acrylate, trimethylol propane tri(meth)acrylate, pentaerythritol di(meth)acrylate, pentaerythritol tri(meth)acrylate, pentaerythritol tetra(meth)acrylate, dipentaerythritol hexa(meth)acrylate and glycerol (meth)acrylate.

In the present invention, the monomer and/or oligomer of the component (D) can be used alone or in combination two or more kinds thereof. These monomers and oligomers can be used as long as the qualities of the color-changing material composition and the color-changing film of the present invention are not damaged, and the amount thereof is usually 10 to 200 parts by weight per 100 parts by weight of the methacrylic acid ester-methacrylic acid copolymer (C). If an amount of the component (D) is 200 parts by weight or less, problems are not brought about on the tacking property after pre-curing.

The color-changing material composition of the present invention further contains preferably (E) a compound having an epoxy group in addition to the components (A) and (B) or the components (A) to (D), and phenol novolak type epoxy compounds and cresol novolak type epoxy compounds can be given as the above compound. The film strength is raised by adding the above compounds to the color-changing material composition when a color-changing film is produced from it. Heating after photopolymerization of the component (D) makes it possible to further cross-link the optically cross-linked product with the compound (E) having an epoxy group to elevate a cross-linking density of the film.

A content of the compound (E) having an epoxy group is preferably 0.1 to 15% by weight, more preferably 0.5 to 7% by weight based on the whole amount of the color-changing material composition. If it is 15% by weight or less, the compound having an epoxy group is not polymerized during storage of the color-changing material composition, and a viscosity of the liquid is not varied. If it is 0.1% by weight or more, the satisfactory effect is obtained.

A photopolymerization initiator or a sensitizer may be added, if necessary, to the color-changing material composition of the present invention, and the photopolymerization initiator and the sensitizer are used not only for optical curing reaction of the monomer and/or oligomer of the component (D) having a photopolymerizable, ethylenically unsaturated group but also as a polymerization initiator for other photopolymerizable compounds blended if necessary. For example, acetophenones, benzophenones, benzoin ethers, sulfur compounds, anthraquinones, organic peroxides and thiols are suitably used as the above photopolymerization initiator. To specifically give the examples thereof, the acetophenones include acetophenone, 2,2-diethoxyacetophenone, p-methylacetophenone, p-dimethylaminopropiophenone, dichloroacetophenone, trichloroacetophenone and p-t-butylacetophenone; the benzophenones include benzophenone, 2-chlorobenzophenone and p,p'-bisdimethylaminobenzophenone; the benzoin ethers include benzyl, benzoin, benzoin methyl ether, benzoin isopropyl ether and benzoin isobutyl ether; the sulfur compounds include benzyl methyl ketal, thioxanthone, 2-chlorothioxanthone, 2,4-diethylthioxanthone, 2-methylthioxanthone and 2-isopropylthioxanthone; the anthraquinones include 2-ethylanthraquinone, octamethylanthraquinone, 1,2-benzanthraquinone and 2,3-diphenylanthraquinone; the organic peroxide compounds include azobisisobutyronitrile, benzoyl peroxide and cumene peroxide; and the thiols include 2-mercaptobenzoxazole and 2-mercaptobenzothiazole. Only one kind of the above photopolymerization initiators and sensitizers can be used alone, and they can be used in combination of two or more kinds thereof.

Further, a compound which does not act as the photopolymerization initiator and the sensitizer in itself but can increase the abilities of the photopolymerization initiator and the sensitizer by using in combination with the compounds described above can be added as well. Such compound includes, for example, tertiary amines such as triethanolamine which exert an effect by using in combination with benzophenone.

A preferred use amount of the above photopolymerization initiators and sensitizers is 0 to 10 parts by weight per 100 parts by weight of the component (D). If the use amount is 10 parts by weight or less, light is liable to reach the inside, and the uncured part is not produced. In addition, an adhesion between a substrate and the resin is good, and a fluorescence of the coloring matter is not reduced.

Further, transparent resins such as oligomers or polymers of melamine resins, phenol resins, alkid resins, polyurethane resins, polyester resins and polyamide resins, polyvinyl alcohol, polyvinylpyrrolidone, hydroxyethyl cellulose, carboxymethyl cellulose, aromatic sulfonamide resins, urea resins and benzoguanamine resins can be added to the color-changing material composition of the present invention in order to raise a fluorescence yield of the fluorescent coloring matter, and the melamine resins and the benzoguanamine resins are particularly preferred. The above resins can be used as long as the properties of the color-changing material composition and the color-changing film are not damaged. The preferred use amount thereof is 200 parts by weight or less, more preferably 100 parts by weight or less per 100 parts by weight of the methacrylic acid ester-methacrylic acid copolymer of the component (C). If the use amount is 200 parts by weight or less, problems are not likely to be brought about on the tacking property after pre-curing.

The color-changing material composition of the present invention can be blended, if necessary, with additives such as curing accelerator, a heat polymerization inhibitor, a plasticizer, a filler, a solvent, a defoaming agent and a leveling agent. The curing accelerator includes, for example, perbenzoic acid derivatives, peracetic acid and benzophenones; the heat polymerization inhibitor includes, for example, hydroquinone, hydroquinone monomethyl ether, pyrogallol, t-butylcatechol and phenothiazine; the plasticizer includes, for example, butyl terephthalate, dioctyl terephthalate and tricresyl; the filler includes, for example, glass fiber, silica, mica and alumina; and for example, phosphorus base, fluorine base and acryl base compounds can suitably be used as the defoaming agent and the leveling agent.

The color-changing film of the present invention shall be explained below.

The color-changing film of the present invention comprises the color-changing material composition of the present invention described above, and the color-changing material composition described above is used to be turned into a film, or the color-changing film can be formed on a substrate by means of coating thereon. In particular, the color-changing film having a desired pattern can be formed at a good accuracy by using a photolithography method.

A solvent used in dissolving various components used for the color-changing material composition in a solvent according to the production processes for the color-changing film is preferably ketones, esters or lactones. The ketones include methyl ethyl ketone, methyl isobutyl ketone and cyclohexane, and the esters include 2-acetoxy-1-ethoxypropane, methyl cellosolve, ethyl cellosolve, butyl cellosolve and cellosolve acetate. The lactones include γ-butyrolactone and the like.

In producing the color-changing film of the present invention by a photolithography method, a solution produced from the photosensitive color-changing material composition described above is usually coated on the surface of a substrate in the form of a solution, and then the solvent is dried (pre-baked) by pre-curing. Thereafter, a photomask is applied on the coating film thus obtained and irradiated with active light to cure an exposed part, and development in which a non-exposed part is eluted by using a weak alkaline aqueous solution is further carried out to form a pattern, followed by further carrying out post-baking for after-drying.

The substrate on which the solution of the color-changing material composition is coated is preferably a flat substrate in which a transmittance of light in a visible area of 400 to 700 nm is 50% or more. To specific, a glass substrate and a polymer plate are used therefor. In particular, soda lime glass, barium•strontium-containing glass, lead glass, aluminosilicate glass, borosilicate glass, barium borosilicate glass or quartz can suitably be used as the glass substrate. The polymer plate includes polycarbonate, acryl, polyethylene terephthalate, polyether sulfide or polysulfone. Any of methods using a roller coater, a land coater and a spinner in addition to a publicly known solution impregnating method and spray method can be used as a method for coating the solution of the color-changing material composition of the present invention on the substrate. A coating film is formed by removing (pre-baking) the solvent after coating in a desired thickness.

This pre-baking is carried out by heating by means of an oven and a hot plate. The heating temperature and the heating time in pre-baking are suitably selected according to the solvent used, and it is carried out, for example, at a temperature of 80 to 150° C. for 1 to 30 minutes. Exposure carried out after pre-baking is carried out by means of an exposure machine, and only a resist of a part corresponding to a pattern is sensitized by carrying out exposure via a photomask. The exposure machine and the exposure irradiation conditions can suitably be selected, and visible rays, UV rays, X-rays and electron beams can be used as the irradiated light. The dose shall not specifically be restricted and is selected in a range of, for example, 1 to 3000 $mJ/cm^2$.

Alkali development after exposure is carried out for the purpose of removing the resist of a part which is not exposed, and a desired pattern is formed by this development. Aqueous solutions of, for example, carbonates of alkaline metals and alkaline earth metals can be used as a developing solution suited to the above alkali development. In particular, the development is preferably carried out at a temperature of 10 to 50° C., preferably 20 to 40° C. using a weak alkaline aqueous solution containing 1 to 3% by weight of carbonate such as sodium carbonate, potassium carbonate and lithium carbonate, and fine images can precisely be formed by means of a commercial developing machine and supersonic washing machine.

The development is carried out in the manner described above, and then heat treatment (post-baking) is carried out on the conditions of 80 to 220° C. and 10 to 120 minutes. This post-baking is carried out in order to raise an adhesion between the color-changing film subjected to patterning and the substrate. This is carried out by heating by means of an oven and a hot plate as is the case with pre-baking.

When the binder material is a thermoplastic resin or a thermosetting resin, an exposing step is not required. The film of the thermosetting resin is cured by carrying out heat treatment (post-baking) after pre-baking.

A film thickness required for changing a wavelength of an incident light to a desired wavelength has to be suitably selected for a film thickness of the color-changing film of the present invention, and the film thickness falls in a range of preferably 1 to 100 µm, more preferably 1 to 20 µm.

The color-changing film of the present invention can be equipped with a color filter in order to obtain a desired wavelength to control a color purity. For example, perylene base pigments, lake pigments, azo base pigments, quinacridone base pigments, anthraquinone base pigments, anthracene base pigments, isoindoline base pigments, isoindolinone base pigments, phthalocyanine base pigments, triphenylmethane basic pigments, indanthrone base pigments, indophenol base pigments, cyanine base pigments and dioxazine base pigments can suitably be used alone or in the form of coloring matters comprising mixtures of two or more kinds thereof, or in the form of solid matters obtained by dissolving or dispersing the coloring matters in binder resins.

The examples of a structure assumed when the color-changing film of the present invention is actually used shall be shown below:

(1) light source/color-changing film
(2) light source/substrate/color-changing film
(3) light source/color-changing film/substrate
(4) light source/light-transmitting substrate/color-changing film/substrate
(5) light source/color-changing film/color filter
(6) light source/substrate/color-changing film/color filter
(7) light source/color-changing film/substrate/color filter
(8) light source/substrate/color-changing film/substrate/color filter
(9) light source/substrate/color-changing film/color filter/substrate
(10) light source/color-changing film/color filter/substrate In using the structures described above, the respective structural elements may be laminated in order or may be stuck together. The order of lamination in the above color-changing film shall not specifically be restricted and may be carried out from either direction, and it may be prepared from the left side to the right side or from the right side to the left side.

The color-changing film of the present invention preferably absorbs a light of a light source to emit a light having a longer wavelength, and an organic EL element, LED (light-emitting diode), a cold-cathode tube, an inorganic EL element, a fluorescent lamp or an incandescent lamp is used as the light source described above, and the organic EL element and the LED element which emit less UV rays deteriorating coloring matters are particularly preferred.

Next, the present invention shall be explained in further details with reference to examples and comparative examples, but the present invention shall by no means be restricted by these examples.

Various evaluations of the color-changing films carried out in the following examples were carried out in the following manners.

(1) Evaluation of Color-changing Performance

A specific example of a case where a color-changing film is combined with an organic EL element to constitute a colorized organic EL element is shown in FIG. 1. As shown in the same drawing, the colorized organic EL element comprises, looking from a light-outgoing side, a glass substrate 1, a color-changing film 2, an anode 3, an organic EL luminescent layer 4 and a cathode 5. The organic EL luminescent layer 4 is liable to be deteriorated in the presence of moisture and oxygen, and therefore it is sealed from a cathode 5 side by means of an opposed glass substrate so that the whole element part including the color-changing film is covered.

In the colorized organic EL element having the above structure, the performances of the individual elements are scattered, and organic EL-emitting light itself which is an excited light has a half life, so that it is difficult to evaluate distinctively only a fluorescent performance and a durability of the color-changing film itself.

Figure 2:
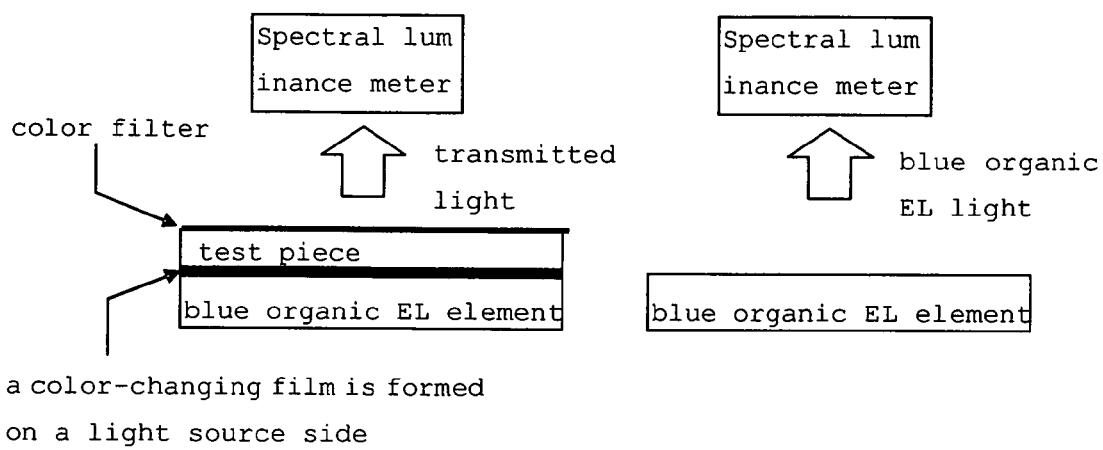
FIG. 2 is a drawing explaining an evaluating method of a color-changing performance in the examples and the comparative examples.

Then, as shown in FIG. 2, a test piece prepared by forming a color-changing film on a transparent glass plate was prepared, and a blue organic EL element separately prepared which has a peak wavelength suitably selected in a range of 440 to 470 nm according to a coloring matter used for the color-changing film was superposed thereon and irradiated with a blue light to measure a spectrum of a transmitted light obtained through the color-changing film and a color filter in a two degree visual field by means of a spectral luminance meter (CS-1000 manufactured by Minolta Co., Ltd.).

It was compared with a luminous spectrum of the blue organic EL element to identify a relative fluorescent intensity of the color-changing film in the following manner:

color-changing efficiency=(luminance of transmitted light obtained through the color-changing film and the color filter)/(luminance of the EL element)

Further, the color coordinate was determined from the measured spectrum.

The performances of the color-changing films can be compared with each other in the manner described above by using the same EL element.

Figure 3:
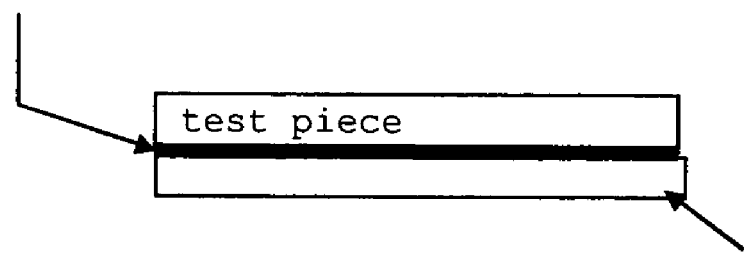
FIG. 3 is a drawing explaining an evaluating method of a chromaticity-holding rate in the examples and the comparative examples.

(2) Excited Light Continuous Irradiation Test (Evaluation of Coloring Matter-holding Rate) onto Color-changing Film Since the EL element has a half life of a luminous intensity, a blue organic EL element having a peak in a wavelength of 470 nm was used as an exited light source having a constant intensity, and the exited light source and the color-changing film (the test piece prepared in (1)) were arranged, as shown in FIG. 3, in a nitrogen-substitutable chamber so that it was bought into contact with the light source, and they were left under dry nitrogen atmosphere to continuously light the blue organic EL element at 400 nit for 1000 hours.

The coloring matter-holding rate was calculated by comparing the absorbances (absorbances originating in coumarin 6 in the case of the comparative examples) of the coloring matter in the test piece before and after irradiated with a blue light.

SYNTHETIC EXAMPLE 1

Synthesis of Compound (I-a)

Sodium 1,2-naphthoquinone-4-sulfonate 1.0 g (3.8 mmol) and $CuCl_2$ 0.26 g (1.92 mmol) were put in a mortar and dissolved in a small amount of an acetic acid aqueous solution. Then, m-(dibutylamino)phenol 0.85 g (3.84 mmol) which was dissolved in a small amount of an acetic acid aqueous solution was added thereto to mix them in the mortar. After the mixture was left standing for several days to react them, water was added thereto, and the deposit was filtered and dried under reduced pressure.

The above deposit was extracted with dichloromethane, and then dichloromethane in the extract was concentrated. The remaining liquid was subjected to silica gel column (developing solvent: dichloromethane/ethyl acetate volume ratio 6/1) to carry out separation and refining, whereby purple powder-like crystal 586 mg (yield 40.9%) which was the intended compound (I-a) was obtained.

The analytical results of the above compound are shown below.

(1) Melting point: 149 to 153° C.

(2) $^1$H-NMR ($CDCl_3$): δ (ppm) 1.00 (6H, t), 1.37 to 1.50 (4H, m), 1.62 to 1.74 (4H, m), 3.34 (4H, t), 6.65 (1H, s) 6.80 (1H, dd), 7.43 (1H, dt), 7.65 (1H, dt), 7.88 (1H, d), 7.93 (1H, d), 8.11 (1H, d)

(3) Infrared absorption spectrum (IR; KBr): 1618 $cm^{-1}$ (4) Element analytical value

|  | C | H | N |
| --- | --- | --- | --- |
| Measured value (%) | 76.91 | 6.83 | 3.76 |
| Calculated value (%) | 76.77 | 6.71 | 3.73 |

(5) Light absorption and fluorescent characteristic (measuring solvent: 1,4-dioxane)

Light absorption characteristic; $\lambda_{max}$ ($\epsilon_{max}$/$dm^3mol^{-1}$ $cm^{-1}$): 410 nm (7800), 533 nm (10800)

Fluorescent characteristic: no fluorescence

SYNTHETIC EXAMPLE 2

Synthesis of Compounds (V-a) and (VI-a)

The compound (I-a) 0.8 g (2.13 mmol) and p-cyanobenzaldehyde 0.42 g (3.16 mmol) were dissolved in acetic acid 60 ml, and ammonium acetate 2.63 g (34.1 mmol) was added thereto to react them at 90° C. for 2 hours. After finishing the reaction, water was added thereto, and dichloromethane was further added to extract the product. The dichloromethane layer was separated and concentrated after washed with water, and the remaining liquid was subjected to silica gel column (developing solvent: xylene/acetic acid volume ratio 20/1) to carry out separation and refining.

Orange powder-like crystal 521 mg (yield 50.2%) which was the compound (V-a) and yellow powder-like crystal 266 mg (yield 25.7%) which was the compound (VI-a) were obtained.

The analytical results of the compound (V-a) and the compound (VI-a) are shown below.

<Compound (V-a)>

(1) Melting point: 203 to 204° C.

(2) $^1$H-NMR ($CDCl_3$): δ (ppm) 1.00 (6H, t), 1.37 to 1.50 (4H, m), 1.62 to 1.74 (4H, m), 3.34 (4H, t), 6.85 (1H, dd), 6.95 (1H, ds), 7.66 (2H, m), 7.81 (2H, d), 8.15 (1H, d), 8.41 (2H, d), 8.60 (1H, d), 8.64 (1H, d), (3) Infrared absorption spectrum (IR; KBr): 1507, 1632, 2226 $cm^{-1}$ (4) Elemental analysis

|  | C | H | N |
| --- | --- | --- | --- |
| Measured value (%) | 78.58 | 5.75 | 8.70 |
| Calculated value (%) | 78.83 | 6.00 | 8.62 |

(5) Light absorption and fluorescent characteristic (measuring solvent: 1,4-dioxane)

Light absorption characteristic; $\lambda_{max}$ ($\epsilon_{max}$/$dm^3mol^{-1}$ $cm^{-1}$): 362 nm (14000), 420 nm (28900)

Fluorescent characteristic: $\lambda_{em}$: 526 nm

<Compound (VI-a)>

(1) Melting point: 227 to 229° C.

(2) $^1$H-NMR ($CDCl_3$): δ (ppm) 1.01 (6H, t), 1.39 to 1.49 (4H, m), 1.62 to 1.72 (4H, m), 3.42 (4H, t), 6.85 (1H, d), 7.00 (1H, ds), 7.65. (1H, t), 7.71 (1H, t), 7.85 (2H, d), 8.13 (1H, d), 8.40 (1H, d), 8.48 (2H, d), 8.65 (1H, d)

(3) Infrared absorption spectrum (IR; KBr): 1505, 1633, 2228 $cm^{-1}$ (4) Element analytical value

|  | C | H | N |
|---|---|---|---|
| Measured value (%) | 78.83 | 5.90 | 8.63 |
| Calculated value (%) | 78.83 | 6.00 | 8.62 |

(5) Light absorption and fluorescent characteristic (measuring solvent: 1,4-dioxane)

Light absorption characteristic; $\lambda_{max}$ ($\epsilon_{max}$/dm$^3$mol$^{-1}$cm$^{-1}$): 366 nm (26800), 418 nm (4500)

Fluorescent characteristic: $\lambda_{em}$: 553 nm

SYNTHETIC EXAMPLE 3

Synthesis of Compounds (V-b) and (VI-b)

The compound (I-a) 0.8 g (2.13 mmol) and 9-anthraldehyde 1.10 g (5.33 mmol) were dissolved in acetic acid 150 ml, and ammonium acetate 8.21 g (0.107 mol) was added thereto to react them at 80° C. for 2 hours. After finishing the reaction, water was added thereto, and dichloromethane was further added to extract the product. The dichloromethane layer was separated and concentrated after washed with water, and the remaining liquid was subjected to silica gel column (developing solvent: xylene/acetic acid volume ratio 20/1) to carry out separation and refining.

Red crystal 823 mg (yield 30.6%) which was the compound (V-b) and orange crystal 585 mg (yield. 21.7%) which was the compound (VI-b) were obtained.

The analytical results of the compound (V-b) and the compound (VI-b) are shown below.

<Compound (V-b)>

(1) Melting point: 112 to 114° C.

(2) $^1$H-NMR (acetone-d$^6$): δ (ppm) 1.00 (6H, t), 1.42 to 1.51 (4H, m), 1.67 to 1.75 (4H, m), 3.51 (4H, q), 7.03 (1H, dd), 7.09 (1H, d), 7.63 to 7.67 (4H, m), 7.78 to 7.87 (2H, m), 8.27 to 8.30 (4H, m), 8.40 (1H, d), 8.76 (1H, d), 8.86 (1H, d), 8.95 (1H, s)

(3) Infrared absorption spectrum (IR; KBr): 1506, 1632 cm$^{-1}$ (4) Elemental analysis

|  | C | H | N |
|---|---|---|---|
| Measured value (%) | 83.36 | 6.14 | 5.02 |
| Calculated value (%) | 83.24 | 6.09 | 4.98 |

(5) Light absorption and fluorescent characteristic (measuring solvent: 1,4-dioxane)

Light absorption characteristic; $\lambda_{max}$ ($\epsilon_{max}$/dm$^3$mol$^{-1}$cm$^{-1}$): 373 nm (26800), 420 nm (14400)

Fluorescent characteristic: $\lambda_{em}$: 569 nm

<Compound VI-b>

(1) Melting point: 175 to 176° C.

(2) $^1$H-NMR (acetone-d$^6$): δ (ppm) 1.02 (6H, t), 1.43 to 1.55 (4H, m), 1.69 to 1.77 (4H, m), 3.52 (4H, q), 7.02 (1H, dd), 7.14 (1H, d), 7.63 to 7.67 (4H, m), 7.72 to 7.76 (1H, m), 7.83 to 7.87 (1H, m), 8.25 to 8.30 (4H, m), 8.38 (1H, d), 8.44 (1H, d), 8.87 (1H, d), 8.96 (1H, s)

(3) Infrared absorption spectrum (IR; KBr): 1507, 1634 cm$^{-1}$ (4) Elemental analysis

|  | C | H | N |
|---|---|---|---|
| Measured value (%) | 83.48 | 6.23 | 5.16 |
| Calculated value (%) | 83.24 | 6.09 | 4.98 |

(5) Light absorption and fluorescent characteristic (measuring solvent: 1,4-dioxane)

Light absorption characteristic; $\lambda_{max}$ ($\epsilon_{max}$/dm$^3$mol$^{-1}$cm$^{-1}$): 373 nm (26400)

Fluorescent characteristic; $\lambda_{em}$: 570 nm

SYNTHETIC EXAMPLE 4

Synthesis of Compounds (V-c) and (VI-c)

The compound (I-a) 0.8 g (2.13 mmol) and 1-pyrenecarboxaldehyde 0.98 g (4.26 mmol) were dissolved in acetic acid 150 ml, and ammonium acetate 6.57 g (85 mmol) was added thereto to react them at 80° C. for 1.5 hour. After finishing the reaction, water was added thereto, and dichloromethane was further added to extract the product. The dichloromethane layer was separated and concentrated after washed with water, and the remaining liquid was subjected to silica gel column (developing solvent: xylene/acetic acid volume ratio 20/1) to carry out separation and refining.

Orange crystal 1.117 g (yield 49.4%) which was the compound (V-c) and yellow crystal 0.82 g (yield 36.2%) which was the compound (VI-c) were obtained.

The analytical results of the compound (V-c) and the compound (VI-c) are shown below.

<Compound (V-c)>

(1) Melting point: 222 to 224° C.

(2) $^1$H-NMR (acetone-d$^6$): δ (ppm) 1.04 (6H, t), 1.45 to 1.54 (4H, m), 1.70 to 1.78 (4H, m), 3.53 (4H, q), 7.02 (1H, dd), 7.12 (1H, d), 7.82 to 7.84 (2H, m), 8.19 (1H, t), 8.29 to 8.38 (3H, m), 8.42 to 8.47 (2H, m), 8.51 to 8.55 (2H, m), 8.80 to 8.82 (1H, m), 8.84 to 8.87 (1H, m), 9.11 (1H, d), 10.15 (1H, d)

(3) Infrared absorption spectrum (IR; KBr): 1506, 1635 cm$^{-1}$ (4) Elemental analysis

|  | C | H | N |
|---|---|---|---|
| Measured value (%) | 83.88 | 5.86 | 4.72 |
| Calculated value (%) | 83.93 | 5.84 | 4.77 |

(5) Light absorption and fluorescent characteristic (measuring solvent: 1,4-dioxane)

Light absorption characteristic; $\lambda_{max}$ ($\epsilon_{max}$/dm$^3$mol$^{-1}$cm$^{-1}$): 362 nm (24800), 397 nm (28800), 436 nm (33600)

Fluorescent characteristic; $\lambda_{em}$: 538 nm

<Compound (VI-c)>

(1) Melting point: 225 to 227° C.

(2) $^1$H-NMR (acetone-d$^6$): δ (ppm) 1.04 (6H, t), 1.48 to 1.53 (4H, m), 1.71 to 1.79 (4H, m), 3.53 (4H, q), 7.01 (1H, dd), 7.18 (1H, d), 7.78 to 7.87 (2H, m), 8.20 (1H, t), 8.31 to 8.39 (3H, m), 8.43 to 8.49 (2H, m), 8.53 to 8.57 (2H, m), 8.64 to 8.67 (1H, m), 8.83 (1H, d), 9.21 (1H, d), 10.18 (1H, d)

(3) Infrared absorption spectrum (IR; KBr): 1500, 1635 cm$^{-1}$ (4) Elemental analysis

|  | C | H | N |
|---|---|---|---|
| Measured value (%) | 83.76 | 5.99 | 4.65 |
| Calculated value (%) | 83.93 | 5.84 | 4.77 |

(5) Light absorption and fluorescent characteristic (measuring solvent: 1,4-dioxane)

Light absorption characteristic; $\lambda_{max}$ ($\epsilon_{max}$/dm$^3$mol$^{-1}$cm$^{-1}$): 377 nm (48800), 395 nm (36400)

Fluorescent characteristic; $\lambda_{em}$: 551 nm

SYNTHETIC EXAMPLE 5

Synthesis of Compounds (III-a) and (IV-a)

4-[4-(Dibutylamino)phenyl]-1,2-naphthoquinone 2.00 g (5.54 mmol), p-ethoxybenzaldehyde 0.83 g (5.54 mmol) and ammonium acetate 6.82 g (88.4 mmol) were dissolved in acetic acid 59 ml and refluxed and stirred at 80° C. for 110 minutes. After finishing the reaction, the solution was neutralized by a sodium carbonate aqueous solution, and methylene chloride was added to extract organic matters. The methylene chloride layer was washed with water and then dried up under reduced pressure, and the residue was subjected to silica gel column (developing solvent: dichloromethane/ethyl acetate volume ratio 10/1) to carry out separation and refining.

The compound (III-a) 1.15 g (yield 42.3%) and the compound (IV-a) 0.75 g (yield 27.5%) were obtained.

<Compound (III-a)>

(1) Melting point:

(2) $^1$H-NMR (acetone-d$^6$): δ (ppm) 1.00 (6H, t), 1.40 (4H, m), 1.47 (3H, t), 1.66 (4H, m), 3.35 (4H, t), 4.12 (2H, q), 6.79 (2H, d), 7.03 (2H, d), 7.39 (2H, d)), 7.46 (1H, t), 7.64 (1H, t), 7.65 (1H, s), 8.13 (1H, d), 8.27 (2H, d), 8.62 (1H, d)

(3) Infrared absorption spectrum (IR; KBr):

(4) Elemental analysis

|  | C | H | N |
|---|---|---|---|
| Measured value (%) | 80.67 | 7.16 | 6.57 |
| Calculated value (%) | 80.45 | 7.37 | 6.50 |

(5) Light absorption and fluorescent characteristic (measuring solvent: 1,4-dioxane)

Light absorption characteristic; $\lambda_{max}$ ($\epsilon_{max}$/dm$^3$mol$^{-1}$cm$^{-1}$): 337 nm, 446 nm Fluorescent characteristic; $\lambda_{em}$: 512 nm <Compound (IV-a)>

(1) Melting point:

(2) $^1$H-NMR (acetone-d$^6$): δ (ppm) 1.00 (6H, t), 1.40 (4H, m), 1.46 (3H, m), 1.66 (4H, m), 3.35 (4H, t), 4.14 (2H, q), 6.77 (2H, d), 7.05 (2H, d), 7.38 (2H, d), 7.45 (1H, t), 7.64 (1H, t), 7.77 (1H, s), 8.13 (1H, d), 8.28 (2H, d), 8.33 (1H, d)

(3) Infrared absorption spectrum (IR; KBr):

(4) Elemental analysis

|  | C | H | N |
|---|---|---|---|
| Measured value (%) | 80.63 | 7.02 | 6.72 |
| Calculated value (%) | 80.45 | 7.37 | 6.50 |

(5) Light absorption and fluorescent characteristic (measuring solvent: 1,4-dioxane)

Light absorption characteristic; $\lambda_{max}$ ($\epsilon_{max}$/dm$^3$mol$^{-1}$cm$^{-1}$): 351 nm, 437 nm Fluorescent characteristic; $\lambda_{em}$: 540 nm

SYNTHETIC EXAMPLE 6

Synthesis of Compounds (III-b) and (IV-b)

4-[4-(Dibutylamino)phenyl]-1,2-naphthoquinone 2.00 g (5.54 mmol), 3,4-difluorobenzaldehyde 0.78 g (5.54 mmol) and ammonium acetate 6.82 g (88.4 mmol) were dissolved in acetic acid 59 ml and refluxed and stirred at 80° C. for 2.5 hours. After finishing the reaction, the solution was neutralized by a sodium carbonate aqueous solution, and methylene chloride was added to extract organic matters. The methylene chloride layer was washed with water and then dried up under reduced pressure, and the residue was subjected to silica gel column (developing solvent: dichloromethane/ethyl acetate volume ratio 10/1) to carry out separation and refining.

The compound (III-b) 0.29 g (yield 10.8%) and the compound (IV-b) 0.19 g (yield 7.2%) were obtained.

<Compound (III-b)>

(1) Melting point:

(2) $^1$H-NMR (acetone-d$^6$): δ (ppm) 1.00 (6H, t), 1.43 (4H, m), 1.66 (4H, m), 3.36 (4H, t), 6.77 (2H, d), 7.32 (1H, m), 7.37 (2H, d), 7.49 (1H, t), 7.65 (1H, s), 7.67 (1H, t), 8.08 (1H, m), 8.16 (2H, m), 8.60 (1H, d)

(3) Infrared absorption spectrum (IR; KBr):

(4) Elemental analysis

|  | C | H | N |
|---|---|---|---|
| Measured value (%) | 76.89 | 6.37 | 5.91 |
| Calculated value (%) | 76.67 | 6.43 | 5.77 |

(5) Light absorption and fluorescent characteristic (measuring solvent: 1,4-dioxane)

Light absorption characteristic; $\lambda_{max}$ ($\epsilon_{max}$/dm$^3$mol$^{-1}$cm$^{-1}$): 303 nm, 353 nm Fluorescent characteristic; $\lambda_{em}$: 454 nm <Compound (IV-b)>

(1) Melting point:

(2) $^1$H-NMR (acetone-d$^6$): δ (ppm) 1.00 (6H, t), 1.42 (4H, m), 1.66 (4H, m), 3.36 (4H, m), 6.78 (2H, d), 7.36 (3H, d), 7.49 (1H, t), 7.65 (1H, t), 7.77 (1H, s), 8.17 (3H, m), 8.39 (1H, d)

(3) Infrared absorption spectrum (IR; KBr):

(4) Elemental analysis

|  | C | H | N |
|---|---|---|---|
| Measured value (%) | 77.01 | 6.24 | 5.83 |
| Calculated value (%) | 76.67 | 6.43 | 5.77 |

(5) Light absorption and fluorescent characteristic (measuring solvent: 1,4-dioxane)
Light absorption characteristic; $\lambda_{max}$ ($\epsilon_{max}$/dm$^3$mol$^{-1}$ cm$^{-1}$): 345 nm (16000),
Fluorescent characteristic; $\lambda_{em}$: 466 nm

SYNTHETIC EXAMPLE 7

Synthesis of Compounds (III-c) and (IV-c)

4-[4-(Diethylamino)phenyl]-1,2-naphthoquinone 3.00 g (9.82 mmol) and 1-pyrenecarboxaldehyde 2.26 g (9.82 mmol) were dissolved in acetic acid 150 ml, and ammonium acetate 15.14 g (0.196 mol) was added thereto to react them by heating and refluxing at 80° C. for 1.5 hour. After finishing the reaction, water was added thereto, and dichloromethane was further added to extract the product. The dichloromethane layer was separated and concentrated after washed with water, and the remaining liquid was subjected to silica gel column (developing solvent: xylene/acetic acid volume ratio 20/1) to carry out separation and refining.

Orange crystal 0.253 g (yield 4.9%) which was the compound (III-c) and yellow crystal 0.977 g (yield 19.2%) which was the compound (IV-c) were obtained.

The analytical results of the compound (III-c) and the compound (IV-c) are shown below.

<Compound (III-c)>
(1) Melting point: 187 to 189° C.
(2) $^1$H-NMR (CDCl$_3$): δ (ppm) 1.27 (6H, t), 3.48 (4H, q), 6.85 (2H, d), 7.46 (2H, d), 7.52 to 7.55 (1H, m), 7.72 to 7.76 (1H, m), 7.80 (1H, s), 8.09 (1H, t), 8.13 to 8.20 (3H, m), 8.26 to 8.39 (4H, m), 8.84 (1H, d), 8.98 (1H, d), 10.00 (1H, d)
(3) Infrared absorption spectrum (IR; KBr): 1522, 1609 cm$^{-1}$
(4) Elemental analysis

|  | C | H | N |
|---|---|---|---|
| Measured value (%) | 86.13 | 5.26 | 5.45 |
| Calculated value (%) | 86.02 | 5.46 | 5.42 |

(5) Light absorption and fluorescent characteristic (measuring solvent: 1,4-dioxane)
Light absorption characteristic; $\lambda_{max}$ ($\epsilon_{max}$/dm$^3$mol$^{-1}$ cm$^{-1}$): 278 nm (36700), 404 nm (41500)
Fluorescent characteristic; $\lambda_{em}$: 518 nm <Compound (IV-c)>
(1) Melting point: 211 to 223° C.
(2) $^1$H-NMR (CDCl$_3$): δ (ppm) 1.27 (6H, t), 3.47 (4H, q), 6.68 (2H, d), 7.45 (2H, d), 7.49 to 7.54 (1H, m), 7.67 to 7.71 (1H, m), 7.95 (1H, s), 8.08 (1H, t), 8.13 to 8.21 (3H, m), 8.26 to 8.37 (4H, m), 8.48 (1H, d), 9.02 (1H, d), 9.87 (1H, d)
(3) Infrared absorption spectrum (IR; KBr): 1521, 1609 cm$^{-1}$
(4) Elemental analysis

|  | C | H | N |
|---|---|---|---|
| Measured value (%) | 86.59 | 5.37 | 5.52 |
| Calculated value (%) | 86.02 | 5.46 | 5.42 |

(5) Light absorption and fluorescent characteristic (measuring solvent: 1,4-dioxane)
Light absorption characteristic; $\lambda_{max}$ ($\epsilon_{max}$/dm$^3$mol$^{-1}$ cm$^{-1}$): 273 nm (39200), 395 nm (33300)
Fluorescent characteristic; $\lambda_{em}$: 520 nm

SYNTHETIC EXAMPLE 8

Synthesis of Compound (IV-d)

The same operation as in Synthetic Example 7 was carried out to obtain a compound (IV-d), except that 9-anthraldehyde was substituted for 1-pyrenecarboxaldehyde in Synthetic Example 7.

The analytical results of the compound (IV-d) are shown below.
(1) Melting point: 178 to 180° C.
(2) $^1$H-NMR (acetone-d$^6$): δ (ppm) 1.23 (6H, t), 3.50 (4H), 6.90 (2H, d), 7.42 (2H, d), 7.57 to 7.64 (5H, m), 7.69 to 7.73 (1H, m), 7.89 (1H, s), 8.13 to 8.18 (3H, m), 8.22 to 8.26 (2H, m), 8.32 to 8.34 (1H, m), 8.91 (1H, S)
(3) Infrared absorption spectrum (IR; KBr): 1521, 1609 cm$^{-1}$
(4) Elemental analysis

|  | C | H | N |
|---|---|---|---|
| Measured value (%) | 85.34 | 5.73 | 5.69 |
| Calculated value (%) | 85.60 | 5.77 | 5.85 |

(5) Light absorption and fluorescent characteristic (measuring solvent: 1,4-dioxane)
Light absorption characteristic; $\lambda_{max}$ ($\epsilon_{max}$/dm$^3$mol$^{-1}$ cm$^{-1}$): 333 nm (12800), 350 nm (12900), 371 nm (12800), 386 nm (12800),
Fluorescent characteristic; $\lambda_{em}$: 547 nm A light absorption and a fluorescent characteristic (measuring solvent: 1,4-dioxane) of the following compound (III-e) are shown:

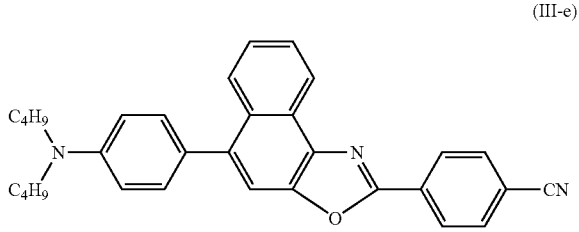

(III-e)

<Compound (III-e)>
Light absorption characteristic;
$\lambda_{max}$($\epsilon_{max}$/dm$_3$mol$^{-1}$ cm$^{-1}$): 385 nm (21800)
Fluorescent characteristic; $\lambda_{em}$: 513 nm

SYNTHETIC EXAMPLE 9

Synthesis of Compound (I-d)

The following compound (I-d) (9-(cyclohexylmethyl-hexyl-amino)benzo[b]naphtho[1,2-d]furan-5,6-dione) was synthesized in the following manner.

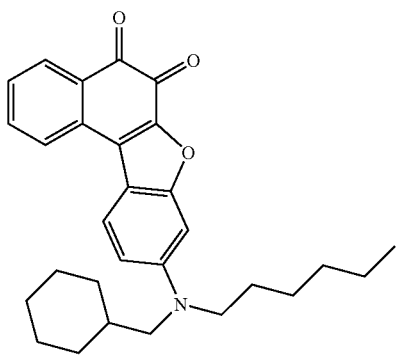

(I-d)

Sodium 1,2-naphthoquinone-4-sulfonate (1.0 g, $3.84\times10^{-3}$ mol), 3-(cyclohexylmethyl-hexyl-amino)phenol (1.11 g, $3.84\times10^{-3}$ mol) and $CuCl_2$ (0.52 g, $3.84\times10^{-3}$ mol) were dissolved in acetic acid 15 ml, and the solution was heated and stirred at 40° C. for 3 hours. After finishing the reaction, water was added thereto, and dichloromethane was further added to extract the product. The dichloromethane layer was separated and concentrated after washed with water, and the remaining liquid was subjected to silica gel column (developing solvent: dichloromethane/ethyl acetate=20/1) to carry out separation and refining, whereby green powder-like crystal 0.135 g (yield 8%) of the compound (I-d) was obtained.

The analytical results of the compound (I-d) (Mw=433.25) are shown below.

(1) Melting point:
(2) $^1$H-NMR (acetone-d$^6$): δ (ppm) 0.89 to 0.94 (5H, m), 1.34 to 1.40 (11H, m), 1.66 to 1.83 (6H, m), 3.34 (2H, d), 3.57 (2H, t), 6.84 (1H, d), 7.07 (1H, dd), 7.55 (1H, td)), 7.78 (1H, td), 8.04 (1H, dd), 8.14 (1H, d), 8.23 (1H, d)

SYNTHETIC EXAMPLE 10

Synthesis of Compound (V-d)

The following compound [in Formula (V), $R^1$=hexyl, $R^2$=cyclohexylmethyl, X=O, Y=O, Ar=benzene ring and substituent of Ar=CN] was synthesized in the following manner.

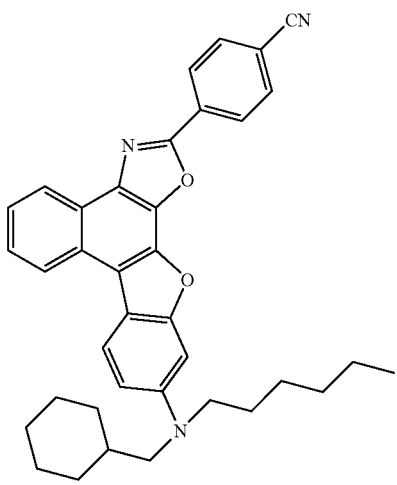

(V-d)

The foregoing compound (I-d) (9-(cyclohexylmethyl-hexyl-amino)benzo[b]naphtho[1,2-d]furan-5,6-dione) (0.135 g, $3.04\times10^{-4}$ mol) and p-cyanobenzaldehyde (0.048 g, $3.66\times10^{-4}$ mol) were dissolved in acetic acid 20 ml, and ammonium acetate (0.375 g, $4.86\times10^{-3}$ mol) was added thereto to react them at 90° C. for 10 hours. After finishing the reaction, water was added thereto, and dichloromethane was further added to extract the product. The dichloromethane layer was separated and concentrated after washed with water, and the remaining liquid was subjected to silica gel column (developing solvent: dichloromethane) to carry out separation and refining, whereby yellow crystal 0.04 g (yield 23.5%) of the compound (V-d) was obtained.

The analytical results of the compound (V-d) (Mw=533.31) are shown below.

(1) Melting point:
(2) $^1$H-NMR (acetone-d$^6$): δ (ppm) 0.89 to 0.96 (5H, m), 1.29 to 1.48 (11H, m), 1.61 to 1.89 (6H, m), 3.36 (2H, d), 3.54 (2H, t), 7.01 (1H, dd), 7.07 (1H, d), 7.65 to 7.68 (1H, m), 7.74 to 7.81 (1H, m), 8.06 to 8.08 (2H, m), 8.32 (1H, d), 8.52 to 8.54 (2H, m), 8.65 (1H, d), 8.76 (1H, d)

SYNTHETIC EXAMPLE 11

Synthesis of Phenylnaphthoxazole Fluorescent Coloring Matters [Compound 1; in Formula (III), $R^1$=$R^2$=ethyl, Y=O, Ar=benzene Ring and Substituent of Ar=CN], [Compound 2; in Formula (IV), $R^1$=$R^2$=ethyl, Y=O, Ar=benzene Ring and Substituent of Ar=CN]

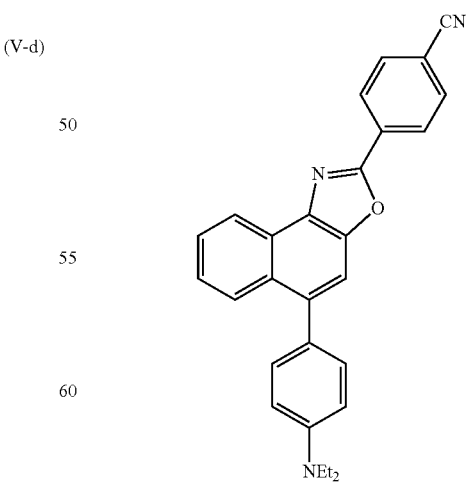

Compound 1

-continued

Compound 2

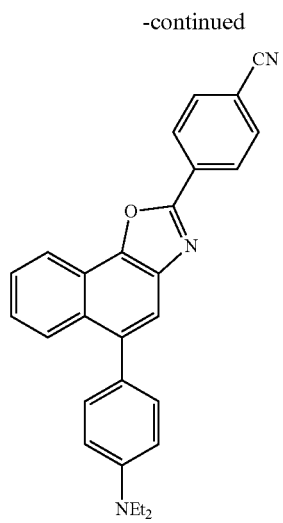

4-[4-(Diethylamino)phenyl]-1,2-naphthoquinone (2.00 g, 5.54 mmol), p-cyanobenzaldehyde (0.73 g, 5.54 mmol) and ammonium acetate (6.82 g, 88.4 mmol) were dissolved in acetic acid 59 ml and refluxed and stirred at 80° C. for 110 minutes. After finishing the reaction, the solution was neutralized by a sodium carbonate aqueous solution, and methylene chloride was added to extract organic matters. The methylene chloride layer was washed with water and then dried up under reduced pressure, and the residue was subjected to silica gel column (developing solvent: dichloromethane:ethyl acetate=10:1) to carry out separation and refining, whereby powder-like crystals of the compound 1 (0.82 g, yield 35.7%) and the compound 2 (0.59 g, yield 25.4%) were obtained.

SYNTHETIC EXAMPLE 12

(1) Synthesis of 4-[4-(dibutylamino)-2-hydroxyphenyl]-1,2-naphthoquinone (intermediate 1)

Sodium 1,2-naphthoquinone-4-sulfonate (1.0 g, 3.84 mmol), N,N-dibutyl-3-aminophenol (1.28 g, 4.01 mmol) and $NiCl_2$ (0.5 g, 3.84 mmol) were dissolved in dimethylformamide (DMF) 45 ml and heated and stirred at 50° C. for 3 hours. After finishing the reaction, the liquid was poured into 300 ml of ion-exchanged water to filter a deposit. The product was extracted from the filtrate with methylene chloride to concentrate the liquid under reduced pressure, and the remaining liquid was subjected to silica gel column (developing solvent: dichloromethane/ethyl acetate=20/1) to carry out separation and refining, whereby blue powder-like crystal 0.77 g (yield 53.1%) which was 4-[4-(dibutylamino)-2-hydroxyphenyl]-1,2-naphthoquinone (intermediate 1) was obtained.

(2) Synthesis of Compound 6 and Compound 7

The intermediate 1 (2.07 g, 5.49 mmol) and anhydrous copper acetate (995 mg, 5.49 mmol) were dissolved in dimethylsulfoxide (DMSO) 60 ml and heated and stirred at 100° C. for 11 hours. After finishing the reaction, the reaction product was poured into 400 ml of distilled water to filter a deposit, and it was subjected to silica gel column (developing solvent: dichloromethane/ethyl acetate=10/1) to carry out separation and refining, whereby purple powder-like crystal 0.22 g (yield 10.4%) of the compound 6 and blue powder-like crystal 1.27 g (yield 61.7%) of the compound 7 were obtained.

intermediate 1

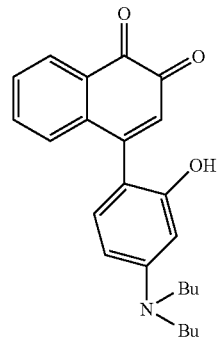

compound 6

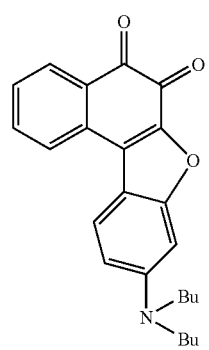

compound 7

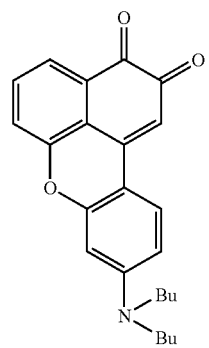

SYNTHETIC EXAMPLE 13

Synthesis of Compound 8 [in Formula (VII), $R^1$=$R^2$=n-butyl, X=O, Y=O and Ar=anthracene Ring]

The compound 7 (1.5 g, 4.00 mmol) and 9-anthraldehyde (0.98 g, 4.79 mmol) were dissolved in acetic acid 120 ml, and ammonium acetate (4.93 g, 64.0 mmol) was added thereto to react them at 105° C. for 15 hours. After finishing the reaction, water was added thereto, and dichloromethane was further added to extract the product. The dichloromethane layer was separated and concentrated after washed with water, and the remaining liquid was subjected to silica gel column (developing solvent: dichloromethane) to carry out separation and refining, whereby red crystal 0.91 g (yield 46.7%) of the compound 8 was obtained.

compound 8

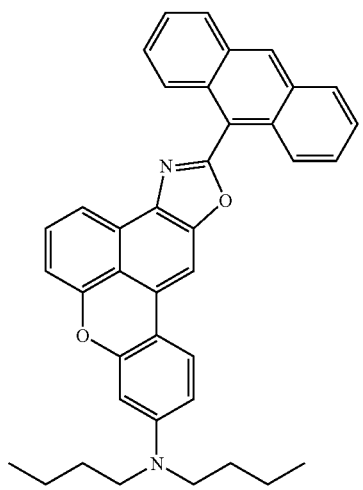

SYNTHETIC EXAMPLE 14

Synthesis of Compound 9 [in Formula (VII), $R^1=R^2$=n-butyl, X=O, Y=O and Ar=pyrene Ring] and Compound 10 [in Formula (VIII), $R^1=R^2$=n-butyl, X=O, Y=O and Ar=pyrene Ring]

The compound 7 (1.5 g, 4.00 mmol) and 1-pyrenecarboxaldehyde (1.10 g, 4.79 mmol) were dissolved in acetcompound 80 ml, and ammonium acetate (4.93 g, 63.9 mmol) was added thereto to react them at 100° C. for 15 hours. After finishing the reaction, water was added thereto, and dichloromethane was further added to extract the product. The dichloromethane layer was separated and concentrated under reduced pressure after washed with water, and the remaining liquid was subjected to silica gel column (developing solvent: xylene/acetic acid=20/1) to carry out separation and refining. Orange crystal 1.12 g (yield 49.4%) of the compound 9 which was a naphthoxazole derivative and yellow crystal 0.82 g (yield 36.2%) of the compound 10 were obtained.

compound 9

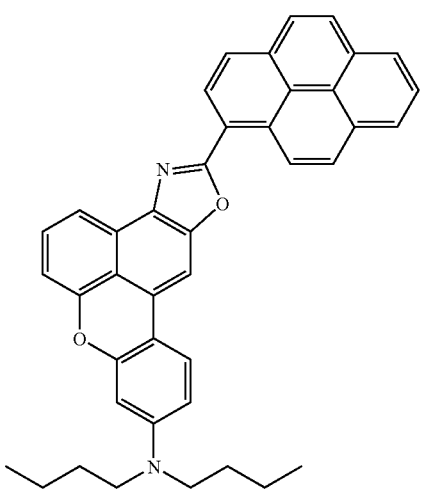

-continued compound 10

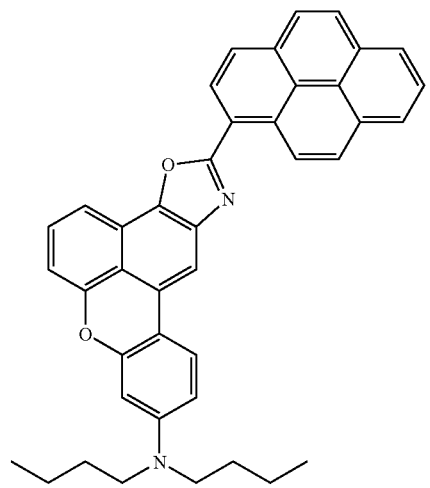

SYNTHETIC EXAMPLE 15

Synthesis of Compound 11 [in Formula (VII), $R^1=R^2$=n-butyl, X=O, Y=O, Ar=benzene Ring and Substituent of Ar=CN], Compound 12 [in Formula (VIII), $R^1=R^2$=n-butyl, X=O, Y=O, Ar=benzene Ring and Substituent of Ar=CN] and Compound 13 [in Formula (VII), $R^1=R^2$=n-butyl, X=O, Y=NH, Ar=benzene Ring and Substituent of Ar=CN]

The compound 7 (0.176 g, 0.47 mmol) and p-cyanobenzaldehyde (0.61 g, 0.47 mmol) were dissolved in acetic acid 8 ml, and ammonium acetate (0.578 g, 7.5 mmol) was added thereto to react them at 80° C. for 7 hours. After finishing the reaction, the reaction product was concentrated under reduced pressure and neutralized with a sodium carbonate aqueous solution to extract the product with dichloromethane. The dichloromethane layer was separated and concentrated under reduced pressure after washed with water, and the remainder was subjected to silica gel column (developing solvent: dichloromethane) to carry out separation, whereby orange crystal 0.074 g (yield 32%) of the compound 13 and the mixture of the compound 11 and the compound 12 were obtained. The mixture of the compound 11 and the compound 12 was subjected to silica gel column (developing solvent: xylene/acetic acid=30/1) to carry out separation and refining, whereby orange crystal 0.02 g (yield 9%) of the compound 11 and yellow crystal 0.019 g (yield 8%) of the compound 12 were obtained.

compound 11

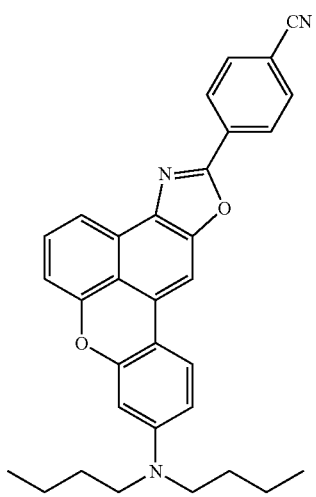

compound 12

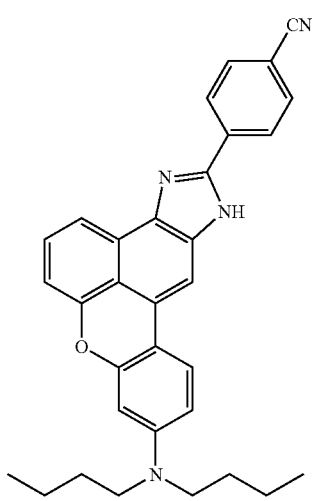

compound 13

SYNTHETIC EXAMPLE 16

Synthesis of Compound 14 [in Formula (VII), $R^1=R^2$=n-butyl, X=O, Y=O, Ar=benzene Ring and Substituent of Ar=$OC_2H_5$]

The compound 7 (2.0 g, 5.3 mmol) and p-ethoxybenzaldehyde (0.96 g, 6.39 mmol) were dissolved in acetic acid 60 ml, and ammonium acetate (6.56 g, 84.3 mmol) was added thereto to react them at 100° C. for 24 hours. After finishing the reaction, the reaction product was concentrated under reduced pressure and neutralized with a sodium carbonate aqueous solution, and dichloromethane was further added to extract the product. The dichloromethane layer was separated and concentrated under reduced pressure after washed with water, and the remainder was subjected to silica gel column (developing solvent: dichloromethane) to carry out separation and refining, whereby yellow crystal 0.978 g (yield 36.5%) of the compound 14 was obtained.

compound 14

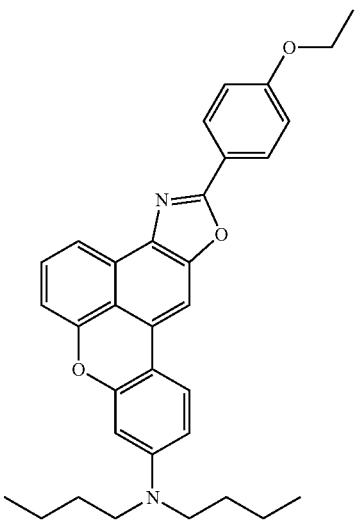

SYNTHETIC EXAMPLE 17

Synthesis of Compound 15 [in Formula (VIII), $R^1=R^2$=n-butyl, X=O, Y=O, Ar=benzene Ring and Substituent of Ar=F]

The compound 7 (1.50 g, 4.00 mmol) and 4-fluorobenzaldehyde (0.56 g, 4.51 mmol) were dissolved in acetic acid 70 ml, and ammonium acetate (4.93 g, 63.9 mmol) was added thereto to react them at 90° C. for 3 hours. After finishing the reaction, the reaction product was concentrated under reduced pressure and neutralized with a sodium carbonate aqueous solution, and the product was extracted with dichloromethane. The dichloromethane layer was separated and concentrated under reduced pressure after washed with water, and the remainder was subjected to silica gel column (developing solvent: xylene/acetic acid=20/1) to carry out separation and refining, whereby 0.22 g (yield 11.8%) of the compound 15 was obtained.

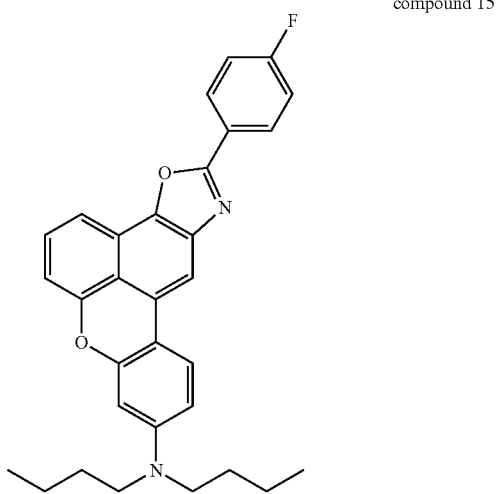

compound 15

EXAMPLES 1 TO 3

(A) a fluorescent coloring matter, (B) a binder material, (C) a binder resin, (D) a monomer and/or oligomer having a photopolymerizable, ethylenically unsaturated group, (E) a compound having an epoxy group and other components (including a solvent) each shown in the following Table 1 were used to prepare color-changing material compositions.

The color-changing material composition thus obtained was used to produce a film on a glass substrate of 2.5 cm×5 cm by a spin coater method. The film was produced on the conditions of a revolution number of 1000 rpm of the spin coater and a revolution time of 10 seconds, and it was subjected to drying treatment at 120° C. for 2 minutes. Thereafter, it was irradiated with UV rays of 300 mJ/cm$^2$ and then subjected to heat treatment at 200° C. for 60 minutes to obtain a color-changing film having a film thickness of 10 µm or less.

The color-changing film thus obtained was used to (1) evaluate a color-changing performance and (2) determine an initial color-changing efficiency and a chromaticity coordinate using a blue EL element having a peak in a wavelength of 440 nm according to a method of an excited light continuous irradiation test (evaluation of a coloring matter-holding rate) onto the color-changing film. Further, the blue EL element was irradiated at 400 nit for 1000 hours, and then a chromaticity and a coloring matter-holding rate thereof were measured. The results thereof are shown in Table 3.

COMPARATIVE EXAMPLES 1 AND 2

Fluorescent coloring matters, a binder material (a binder resin and a monomer and/or oligomer having a photopolymerizable, ethylenically unsaturated group), a compound having an epoxy group and other components (including a solvent) each shown in the following Table 2 were used to prepare color-changing material compositions.

TABLE 1

|  | Example 1 | Example 2 | Example 3 |
| --- | --- | --- | --- |
| Fluorescent coloring matter (A component) | Compound 1 0.072 g | Compound (V-a) 0.034 g | Compound (V-a) 0.034 g Rhodamine 6G 0.017 g Rhodamine B 0.017 g |
| Binder resin (C component) | Benzyl methacrylate-methacrylic acid copolymer (Mw = 27,000, q = 0.80) 1.9 g | Methyl methacrylate-methacrylic acid copolymer (Mw = 25,000, q = 0.85) 1.9 g | Same as in Example 2 |
| Monomer/oligomer (D component) | Dipentaerythritol hexaacrylate (Aronix M-400 manufactured by Toa Gosei) 1.5 g | Trimethylolpropane triacrylate (Aronix M-309 manufactured by Toa Gosei) 1.4 g | Same as in Example 2 |
| Epoxy compound (E component) | Cresol novolak type epoxy resin (ECN 1299 manufactured by Asahi Kasei) 0.20 g | None | None |
| Other components | 2-Acetoxy-1-ethoxy-propane (solvent) 2.5 g Cyclohexanone (solvent) 3.0 g Photopolymerization initiator (Irgacure 907 manufactured by Ciba Specialty Chemicals) 0.035 g | 2-Acetoxy-1-ethoxy-propane (solvent) 2.4 g Cyclohexanone (solvent) 3.0 g Photopolymerization initiator (Irgacure 907 manufactured by Ciba Specialty Chemicals) 0.034 g | Same as in Example 2 |

TABLE 2

|  | Comparative Example 1 | Comparative Example 2 |
| --- | --- | --- |
| Fluorescent coloring matter (A component) | Coumarin 6 0.034 g | Coumarin 6 0.034 g Rhodamine 6G 0.017 g Rhodamine B 0.017 g |
| Binder resin (C component) | Same as in Example 2 | Same as in Example 2 |
| Monomer and/or oligomer (D component) | Same as in Example 2 | Same as in Example 2 |
| Epoxy compound (E component) | None | None |
| Other components | Same as in Example 2 | Same as in Example 2 |

The color-changing material compositions thus obtained were used to obtain color-changing films in the same manner as in Examples 1 to 3, and an initial color-changing efficiency and a chromaticity coordinate thereof were determined. Further, the chromaticity and the coloring matter-holding rate after irradiation were measured. The results thereof are shown in Table 3.

TABLE 3

|  | Initial color-changing efficiency (%) | Chromaticity (initial) | Chromaticity (after irradiated with light) | Coloring matter-holding rate (%) |
| --- | --- | --- | --- | --- |
| Example 1 | 49.6 | 0.23, 0.63 | 0.22, 0.62 | 72.7 |
| Example 2 | 50.3 | 0.25, 0.65 | 0.23, 0.63 | 78.3 |
| Example 3 | 19.2 | 0.64, 0.35 | 0.63, 0.36 | 79.1 |
| Comparative Example 1 | 52.0 | 0.23, 0.63 | 0.20, 0.60 | 49.3 |
| Comparative Example 2 | 19.0 | 0.64, 0.35 | 0.61, 0.37 | 62.1 |

As shown in Table 3, in Comparative Examples 1 and 2, the initial color-changing efficiency stands comparison with those in Examples 1 to 3, but the coloring matter-holding rates are notably inferior, and the color change before and after irradiation is large.

Further, in the color-changing material compositions of the comparative examples, crystals of coumarin 6 have been deposited during storage (refrigerator 5° C.).

EXAMPLES 4 TO 13

(A) a fluorescent coloring matter, (B) a binder material, (C) a binder resin, (D) a monomer and/or oligomer having a photopolymerizable, ethylenically unsaturated group, (E) a compound having an epoxy group and other components (including a solvent) each shown in the following Table 1 were used to prepare color-changing material compositions.

TABLE 4

|  | Example 4 | Example 5 | Example 6 |
| --- | --- | --- | --- |
| Coloring matter (A component) | Compound 11 0.0018 g Compound 12 0.0018 g | Compound 10 0.0035 g | Compound 9 0.0035 g |
| Binder resin (C component) | Methyl methacrylate-methacrylic acid copolymer (Mw = 25,000, q = 0.85) 0.40 g | Benzyl methacrylate-methacrylic acid copolymer (Mw = 27,000, q = 0.80) 0.40 g | Same as in Example 4 |
| Monomer/oligomer (D component) | Pentaerythritol triacrylate (Aronix M-305 manufactured by Toa Gosei) 0.29 g | Trimethylolpropane triacrylate (Aronix M-309 manufactured by Toa Gosei) 0.29 g | Same as in Example 4 |
| Epoxy compound (E component) | None | None | None |
| Other components | 2-Acetoxy-1-ethoxy-propane (solvent) 0.75 g Cyclohexanone (solvent) 0.56 g Photopolymerization initiator (Irgacure 907 manufactured by Ciba Specialty Chemicals) 0.0063 g | Same as in Example 4 | Same as in Example 4 |

TABLE 5

|  | Example | |
|---|---|---|
|  | Example 7 | Example 9 |
| Coloring matter (A component) | Compound 13 0.0035 g | Compound 9 0.0060 g |
| Binder resin (C component) | Same as in Example 4 | Methyl methacrylate-methacrylic acid copolymer (Mw = 25,000, q = 0.87) 0.40 g |
| Monomer/oligomer (D component) | Same as in Example 4 | Same as in Example 4 |
| Epoxy compound (E component) | None | Cresol novolak type epoxy resin (ECN 1299 manufactured by Asahi Kasei) 0.15 g |
| Other components | Same as in Example 4 | Same as in Example 4 |

TABLE 6

|  | Example 9 | Example 10 | Example 11 |
|---|---|---|---|
| Coloring matter (A component) | Compound (V-d) 0.0035 g | Compound (V-c) 0.0021 g | Compound (III-c) 0.0026 g |
| Binder resin (C component) | Methyl methacrylate-methacrylic acid copolymer (Mw = 25,000, q = 0.87) 0.40 g | Same as in Example 9 | Benzyl methacrylate-methacrylic acid copolymer (Mw = 27,000, q = 0.80) 0.40 g |
| Monomer/oligomer (D component) | Pentaerythritol triacrylate (Aronix M-305 manufactured by Toa Gosei) 0.29 g | Same as in Example 9 | Dipentaerythritol hexaacrylate (Aronix M-400 manufactured by Toa Gosei) 0.39 g |
| Epoxy compound (E component) | None | None | Cresol novolak type epoxy resin (ECN 1299 manufactured by Asahi Kasei) 0.023 g |
| Other components | 2-Acetoxy-1-ethoxy-propane (solvent) 0.75 g Tetracholoroethane (solvent) 0.56 g Photopolymerization initiator (Irgacure 907 manufactured by Ciba Specialty Chemicals) 0.0063 g | Same as in Example 9 | 2-Acetoxy-1-ethoxy-propane (solvent) 0.86 g Tetracholoroethane (solvent) 0.28 g Photopolymerization initiator (Irgacure 907 manufactured by Ciba Specialty Chemicals) 0.0044 g |

TABLE 7

|  | Example | |
|---|---|---|
|  | Example 12 | Example 13 |
| Coloring matter (A component) | Compound 8 0.010 g | Same as in Example 9 |
| Binder resin (C component) | Polycarbonate (Mw = 20,000) 1.99 g |  |
| Monomer/oligomer (D component) | None |  |
| Epoxy compound (E component) | None |  |
| Other components | Toluene (solvent) 8.0 g |  |

The color-changing material compositions obtained in Examples 4 to 13 were used to produce films on a glass substrate of 2.5 cm×5 cm by a spin coater method. The films were produced on the conditions of a revolution number of 1000 rpm of the spin coater and a revolution time of 10 seconds, and they were subjected to drying treatment at 120° C. for 2 minutes.

Thereafter, the films produced in Examples 4 to 11 were irradiated with UV rays of 300 mJ/cm$^2$ and then subjected to heat treatment at 200° C. for 60 minutes to obtain color-changing films having a film thickness of 10 μm or less. The film produced in Example 12 was subjected only to heat treatment at 200° C. for 60 minutes. Further, the color-changing material composition prepared in Example 13 was coated on a commercial blue LED element and dried at 70° C.

The color-changing films thus obtained were used to (1) evaluate a color-changing performance and (2) determine an initial color-changing efficiency and a chromaticity coordinate using a blue EL element having a peak in a wavelength of 470 nm according to a method of an excited light continuous irradiation test (evaluation of a coloring matter-holding rate) onto the color-changing film. Further, the blue EL element was irradiated at 400 nit for 1000 hours, and then a chromaticity and a coloring matter-holding rate thereof were measured. The results thereof are shown in Table 8.

TABLE 8

|  | Initial color-changing efficiency (%) | Chromaticity (initial) | Chromaticity (after irradiated with light) | Coloring matter-holding rate (%) |
|---|---|---|---|---|
| Example 4 | 51.0 | 0.23, 0.63 | 0.21, 0.61 | 57.9 |
| Example 5 | 48.5 | 0.23, 0.64 | 0.21, 0.62 | 57.5 |
| Example 6 | 48.7 | 0.24, 0.63 | 0.21, 0.61 | 58.8 |
| Example 7 | 49.9 | 0.22, 0.63 | 0.21, 0.62 | 65.8 |
| Example 8 | 51.1 | 0.24, 0.62 | 0.22, 0.61 | 58.2 |
| Example 9 | 51.5 | 0.22, 0.62 | 0.20, 0.60 | 75.8 |
| Example 10 | 51.9 | 0.23, 0.63 | 0.21, 0.61 | 78.3 |

TABLE 8-continued

| | Initial color-changing efficiency (%) | Chromaticity (initial) | Chromaticity (after irradiated with light) | Coloring matter-holding rate (%) |
|---|---|---|---|---|
| Example 11 | 47.9 | 0.20, 0.60 | 0.20, 0.60 | 79.8 |
| Example 12 | 47.6 | 0.22, 0.62 | 0.21, 0.61 | 73.9 |

The color-changing material compositions obtained in Examples 4 to 12 could stably be stored in a refrigerator of 5° C. Further, green light emission could visually be observed in Example 13.

INDUSTRIAL APPLICABILITY

According to the present invention, capable of being provided is a novel hetero-polycyclic compound which functions as a luminescent material for disperse dyes, coloring maters for ink-jet printing and organic electroluminescent elements or as an organic fluorescent coloring matter having a clathrate-forming ability and a fluorescent property and capable of changing the solid optical properties (color tone and fluorescent property) of coloring matters to a large extent by allowing various organic low molecular compounds (organic guest molecules) to be included therein and which is suitably used for various applications, and coloring matters comprising the above hetero-polycyclic compound and pigments or dyes containing the above hetero-polycyclic compound are useful for various applications and particularly suited as materials for color-changing material compositions.

A color-changing film obtained from the color-changing material composition of the present invention is not deteriorated in a color-changing performance even after used for long time and is prevented from being unusable due to deposition of the coloring matter during storage.

Accordingly, the color-changing film of the present invention is most suited as a color-changing film for fully colorizing organic electroluminescent elements, LED elements and the like.

What is claimed is:

1. A hetero-polycyclic compound represented by the following Formula (I):

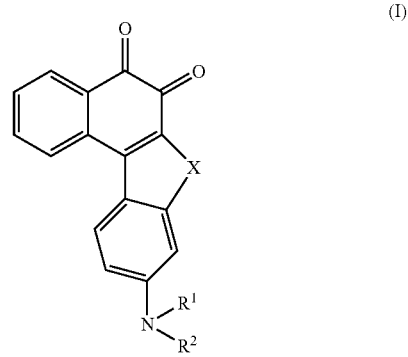

wherein $R^1$ and $R^2$ each represent independently an alkyl group having 1 to 10 carbon atoms which may have a substituent, an arylalkyl group having 7 to 30 carbon atoms which may have a substituent, an aryl group having 6 to 20 carbon atoms which may have a substituent or a heteroaryl group having 5 to 20 carbon atoms which may have a substituent, and they may be combined with each other to form a cyclic structure or may form a cyclic structure together with a benzene ring to which a nitrogen atom is bonded; and X represents an oxygen atom, a sulfur atom, —NH— or —NR$^3$— (R$^3$ represents an alkyl group having 1 to 10 carbon atoms which may have a substituent, an aryl group having 6 to 20 carbon atoms which may have a substituent or a heteroaryl group having 5 to 20 carbon atoms which may have a substituent).

2. A coloring matter comprising the hetero-polycyclic compound as described in claim 1.

3. A pigment or a dye comprising the hetero-polycyclic compound as described in any of claim 1.

* * * * *